United States Patent
Huang et al.

(10) Patent No.: US 7,771,967 B2
(45) Date of Patent: Aug. 10, 2010

(54) NUCLEIC ACID ENCODING APOLIPOPROTEIN E-I3

(75) Inventors: Yadong Huang, San Francisco, CA (US); Qin Xu, Burlingame, CA (US)

(73) Assignee: The J. David Gladstone Institutes, Irvine, CA (US)

( * ) Notice: Subject to any disclaimer, the term of this patent is extended or adjusted under 35 U.S.C. 154(b) by 20 days.

(21) Appl. No.: 11/960,229

(22) Filed: Dec. 19, 2007

(65) Prior Publication Data

US 2009/0011415 A1 Jan. 8, 2009

Related U.S. Application Data

(60) Provisional application No. 60/876,937, filed on Dec. 22, 2006.

(51) Int. Cl.
- *C12P 21/06* (2006.01)
- *C12P 21/04* (2006.01)
- *C12P 1/00* (2006.01)
- *C12P 19/34* (2006.01)
- *C12N 15/00* (2006.01)
- *C12N 1/20* (2006.01)
- *C07H 21/02* (2006.01)
- *A01N 63/00* (2006.01)

(52) U.S. Cl. .................. 435/69.1; 435/71.1; 435/320.1; 435/41; 435/91.1; 435/252.3; 536/23.1; 424/93.2; 424/93.21

(58) Field of Classification Search ........................ None
See application file for complete search history.

(56) References Cited

U.S. PATENT DOCUMENTS 7,435,541 B2 * 10/2008 Olson et al. .................... 435/6

OTHER PUBLICATIONS

Chou et al., "Structural variation in human apolipoprotein E3 and E4: secondary structure, tertiary structure, and size distribution," Biophys. J., 2005, 88(1):455-466.
Huang, "Molecular and cellular mechanisms of apolipoprotein E4 neurotoxicity and potential therapeutic strategies," Curr. Opin. Drug Discov. Devel., 2006, 9(5):627-641.
Huang, "Apolipoprotein E and Alzheimer disease," Neurology, 2006, 66(2 Suppl 1):S79-S85.
Mahley et al., "Apolipoprotein E4: a causative factor and therapeutic target in neuropathology, including Alzheimer's disease," Proc. Natl. Acad. Sci. USA, 2006, 103(15):5644-5651.
Weisgraber, "Apolipoprotein E: structure-function relationships," Adv. Protein Chem., 1994, 45:249-302.
Xu et al., "Profile and regulation of apolipoprotein E (ApoE) expression in the CNS in mice with targeting of green fluorescent protein gene to the ApoE locus," J. Neurosci., 2006, 26(19):4985-4994.

* cited by examiner

*Primary Examiner*—Olga N Chernyshev
(74) *Attorney, Agent, or Firm*—Paula A. Borden; Bozicevic, Field & Francis LLP

(57) ABSTRACT

The present invention provides nucleic acids comprising a nucleotide sequence encoding an apolipoprotein E (apoE) splice variant, e.g., an unprocessed apoE, that retains intron 3; and vectors and host cells comprising same. The present invention further provides screening methods to identify agents that inhibit cleavage of intron-3 from the apoE splice variant. The present invention further provides methods of treating apoE-related neurological disorders, involving administering an agent that inhibits removal of intron-3 from a precursor apoE mRNA.

12 Claims, 12 Drawing Sheets

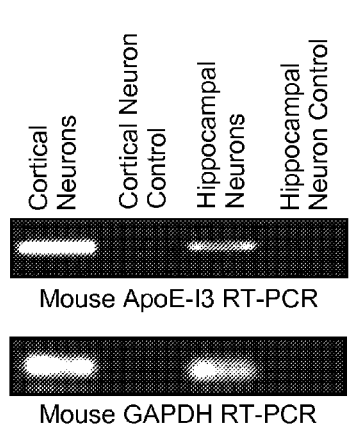
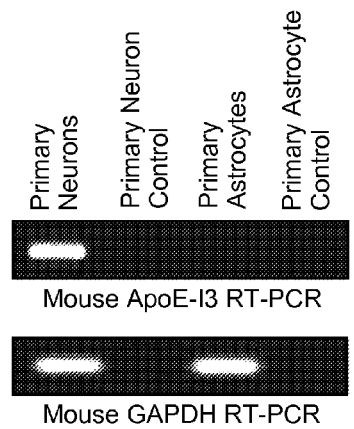
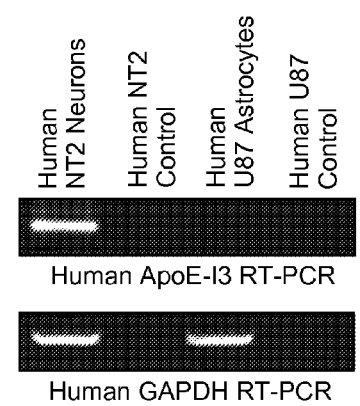
FIG. 2A
FIG. 2B
FIG. 2C
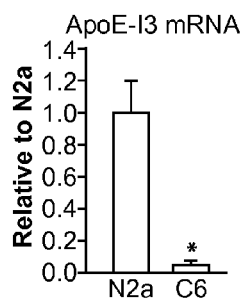
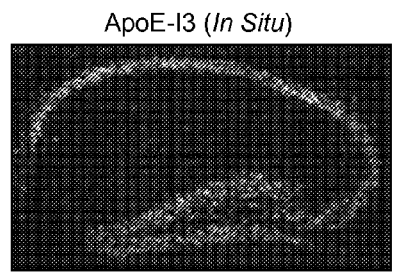
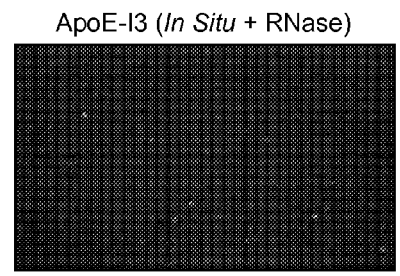
FIG. 2D
FIG. 2E
FIG. 2F

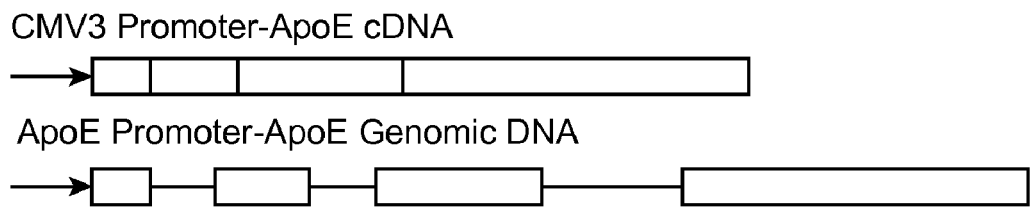
FIG. 4A
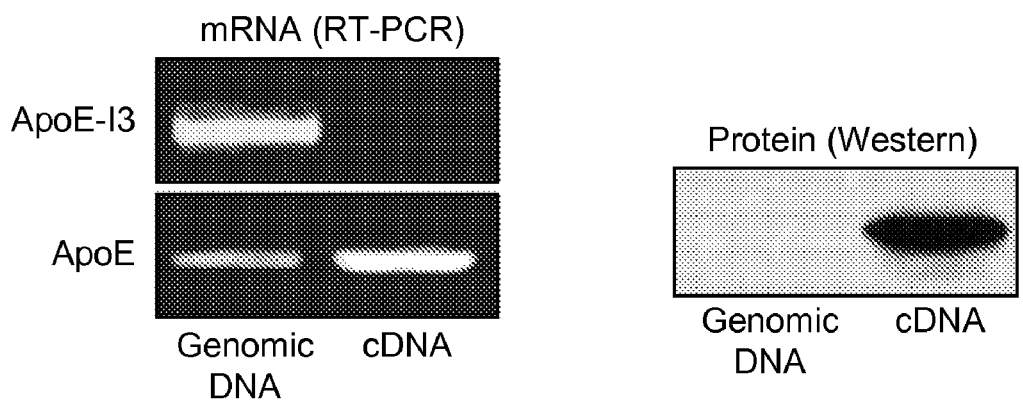
FIG. 4B
FIG. 4C
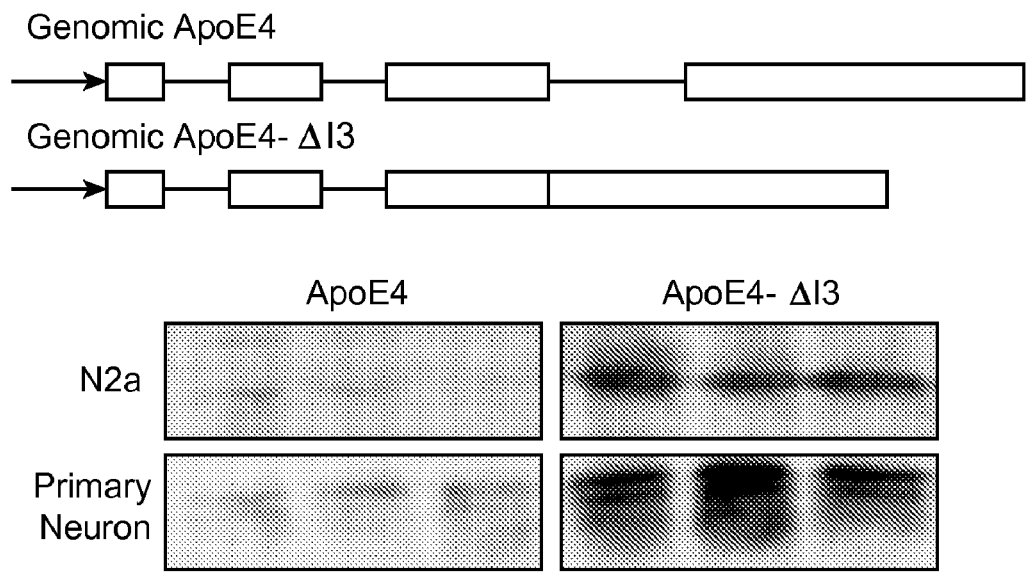
FIG. 4D

Neurons from untreated Mice

Neurons from KA-treated Mice

ApoE-I3 Splicing Mutant

A human apoE-I3 transcript sequence:
Cagcggaggtgaaggacgtccttccccaggagccgactggccaatcacaggcaggaagatgaaggttctgtgggctgcgttgctggtca
cattcctggcaggatgccaggccaaggtggagcaagcggtggagacagagccggagcccgagctgcgccagcagaccgagtggcaga
gcggccagcgctgggaactggcactgggtcgcttttgggattacctgcgctgggtgcagacactgtctgagcaggtgcaggaggagctgct
cagctcccaggtcacccaggaactgaggtgagtgtccccatcctggcccttgaccctcctggtgggcggctatacctccccaggtccaggtt
tcattctgcccctgtcgctaagtcttgggggcctgggtctctgctggttctagcttcctcttcccatttctgactcctggcttagctctctggaatt
ctctctctcagctttgtctctctctcttcccttctgactcagtctctcacactcgtcctggctctgtctctgtccttccctagctcttttatatagagaca
gagagatggggtctcactgtgttgcccaggctggtcttgaacttctgggctcaagcgatcctcccgcctcggcctcccaaagtgctgggatta
gaggcatgagccaccttgcccggcctcctagctccttcttcgtctctgcctctgccctctgcatctgctctctgcatctgtctctgtcctttctctc
ggcctctgccccgttccttctctccctcttgggtctctctggctcatcccatctcgcccgccccatcccagcccttctccccgcctcccactgtg
cgacaccctcccgccctctcggccgcagggcgctgatggacgagaccatgaaggagttgaaggcctacaaatcggaactggaggaacaa
ctgacccggtggcggaggagacgcgggcacggctgtccaaggagctgcaggcggcgcaggcccggctgggcgcggacatggagga
cgtgtgcggccgcctggtgcagtaccgcggcgaggtgcaggccatgctcggccagagcaccgaggagctgcgggtgcgcctcgcctcc
cacctgcgcaagctgcgtaagcggctcctccgcgatgccgatgacctgcagaagcgcctggcagtgtaccaggccggggcccgcgagg
gcgccgagcgcggcctcagcgccatccgcgagcgcctgggggcccctggtggaacagggccgcgtgcgggccgccactgtgggctccc
tggccggccagccgctacaggagcgggcccaggcctgggcgagcggctgcgcgcgcggatggaggagatgggcagccggacccg
cgaccgcctggacgaggtgaaggagcaggtggcggaggtgcgcgccaagctggaggagcaggcccagcagatacgcctgcaggccg
aggccttccaggcccgcctcaagagctggttcgagcccctggtggaagacatgcagcgccagtgggccgggctggtggagaaggtgca
ggctgccgtgggcaccagcgccgcccctgtgcccagcgacaatcactgaacgccgaagcctgcagccatgcgaccccacgccacccg
tgcctcctgcctccgcgcagcctgcagcgggagaccctgtccccgccccagccgtcctcctggggtggaccctagtttaataaagattcacc
aagtttcacgcaaaaaaaaaa (SEQ ID NO:1)

FIG. 10A

A mouse apoE-I3 transcript sequence:
Gctcagaccctggaggctaaggacttgtttcggaaggagctgctggccaatcacaattgcgaagatgaaggctctgtgggccgtgctgttg
gtcacattgctgacaggatgcctagccgagggagagccggaggtgacagatcagctcgagtggcaaagcaaccaaccctgggagcagg
ccctgaaccgcttctgggattacctgcgctgggtgcagacgctgtctgaccaggtccaggaagagctgcagagctcccaagtcacacaaga
actgacgtgagtgtccagctctttcaccctcggcaggcaccagctgatccaggttgcctcctatctgggtccccagcccttcttgtttcctttc
tcaattagtgtgtagcccaggttggccttgaatcctcctgccttctttagccttctggatgctgggaggaacagacatttattacttgcttggtcgat
tggcttttggcttcttgagacaggatcccattctgtaactcaagctggcttcgaaggctctgcaattcttatgccgcagcttctcaacttctgggaa
cacaagcgagtaccatcacctcttgcctctgtggtttctggcccttctgtcctgccttcatctccttcctgtgtttcctctgggcctgcagggcac
tgatggaggacactatgacggaagtaaaggcttacaaaaaggagctggaggaacagctgggtccagtggcggaggagacacgggccag
gctgggcaaagaggtgcaggcggcacaggcccgactcggagccgacatggaggatctacgcaaccgactcgggcagtaccgcaacga
ggtgcacaccatgctgggccagagcacagaggagatacgggcgcggctctccacacacctgcgcaagatgcgcaagcgcttgatgcgg
gatgccgaggatctgcagaagcgcctagctgtgtacaaggcaggggcacgcgagggcgccgagcgcggtgtgagtgccatccgtgagc
gcctggggcctctggtggagcaaggtcgccagcgcactgccaacctaggcgctggggccgcccagcctctgcgcgatcgcgcccaggc
ttttggtgaccgcatccgagggcggctggaggaagtgggcaaccaggcccgtgaccgcctagaggaggtgcgtgagcacatggaggag
gtgcgctccaagatggaggaacagacccagcaaatacgcctgcaggcggagatcttccaggcccgcctcaagggctggttcgagccaat
agtggaagacatgcatcgccagtgggcaaacctgatggagaagatacaggcctctgtggctaccaacccatcatcaccccagtggccca
ggagaatcaatgagtatcttctcctgtcctgcaacaacatccatatccagccaggtggccctgtctcaagcacctctctggccctctggtggc
ccttgcttaataaagattctccgagcacaaaaaaaaaa (SEQ ID NO:2)

FIG. 10B

```
gagcaggtgcaggaggagctgctcagctcccaggtcacccaggaactgaggtgagtgtccccatc
ctggcccttgaccctcctggtgggcggctatacctcccaggtccaggtttcattctgcccctgt
cgctaagtcttggggggcctgggtctctgctggttctagcttcctcttcccatttctgactcctg
gctttagctctctggaattctctctctcagctttgtctctctctcttcccttctgactcagtctc
tcacactcgtcctggctctgtctctgtccttccctagctcttttatatagagacagagagatggg
gtctcactgtgttgcccaggctggtcttgaacttctgggctcaagcgatcctcccgcctcggcct
cccaaagtgctgggattagaggcatgagccaccttgcccggcctcctagctccttcttcgtctct
gcctctgccctctgcatctgctctctgcatctgtctctgtctccttctctcggcctctgccccgt
tccttctctccctcttgggtctctctggctcatccccatctcgcccgcccatcccagcccttct
ccccgcctcccactgtgcgacaccctcccgccctctcggccgcagggcgctgatggacgagacca
tgaaggagttgaaggcctacaaatcggaac (SEQ ID NO:3)
```

FIG. 10C

```
tggcactgggtcgcttttgggattacctgcgctgggtgcagacactgtctgagcaggtgcaggag
gagctgctcagctcccaggtcacccaggaactgaggtgagtgtccccatcctggcccttgaccct
cctggtgggcggctatacctcccaggtccaggtttcattctgcccctgtcgctaagtcttgggg
ggcctgggtctctgctggttctagcttcctcttcccatttctgactcctggctttagctctctgg
aattctctctctcagctttgtctctctctcttcccttctgactcagtctctcacactcgtcctgg
ctctgtctctgtccttccctagctcttttatatagagacagagagatggggtctcactgtgttgc
ccaggctggtcttgaacttctgggctcaagcgatcctcccgcctcggcctcccaaagtgctggga
ttagaggcatgagccaccttgcccggcctcctagctccttcttcgtctctgcctctgccctctgc
atctgctctctgcatctgtctctgtctccttctctcggcctctgccccgttccttctctccctct
tgggtctctctggctcatccccatctcgcccgcccatcccagcccttctccccgcctcccactg
tgcgacaccctcccgccctctcggccgcagggcgctgatggacgagaccatgaaggagttgaagg
cctacaaatcggaactggaggaacaactgacccggtggcggaggagacgcgggcacggctgtcc
```
(SEQ ID NO:4)

FIG. 10D

ApoE-I3-EGFP Reporter Construct

SEQUENCE LISTING

```
<160> NUMBER OF SEQ ID NOS: 20

<210> SEQ ID NO 1
<211> LENGTH: 1744
<212> TYPE: DNA
<213> ORGANISM: Homo sapiens

<400> SEQUENCE: 1
cagcggaggt gaaggacgtc cttccccagg agccgactgg ccaatcacag gcaggaagat      60
gaaggttctg tgggctgcgt tgctggtcac attcctggca ggatgccagg ccaaggtgga     120
gcaagcggtg gagacagagc cggagcccga gctgcgccag cagaccgagt ggcagagcgg     180
ccagcgctgg gaactggcac tgggtcgctt ttgggattac ctgcgctggg tgcagacact     240
gtctgagcag gtgcaggagg agctgctcag ctcccaggtc acccaggaac tgaggtgagt     300
gtccccatcc tggcccttga ccctcctggt gggcggctat acctccccag gtccaggttt     360
cattctgccc ctgtcgctaa gtcttggggg gcctgggtct ctgctggttc tagcttcctc     420
```

```
ttcccatttc tgactcctgg ctttagctct ctggaattct ctctctcagc tttgtctctc      480
tctcttccct tctgactcag tctctcacac tcgtcctggc tctgtctctg tccttcccta      540
gctcttttat atagagacag agagatgggg tctcactgtg ttgcccaggc tggtcttgaa      600
cttctgggct caagcgatcc tcccgcctcg gcctcccaaa gtgctgggat tagaggcatg      660
agccaccttg cccggcctcc tagctccttc ttcgtctctg cctctgccct ctgcatctgc      720
tctctgcatc tgtctctgtc tccttctctc ggcctctgcc ccgttccttc tctccctctt      780
gggtctctct ggctcatccc catctcgccc gccccatccc agcccttctc cccgcctccc      840
actgtgcgac accctcccgc cctctcggcc gcagggcgct gatggacgag accatgaagg      900
agttgaaggc ctacaaatcg gaactggagg aacaactgac cccggtggcg gaggagacgc      960
gggcacggct gtccaaggag ctgcaggcgg cgcaggcccg gctgggcgcg gacatggagg     1020
acgtgtgcgg ccgcctggtg cagtaccgcg gcgaggtgca ggccatgctc ggccagagca     1080
ccgaggagct gcgggtgcgc ctcgcctccc acctgcgcaa gctgcgtaag cggctcctcc     1140
gcgatgccga tgacctgcag aagcgcctgg cagtgtacca ggccggggcc cgcgagggcg     1200
ccgagcgcgg cctcagcgcc atccgcgagc gctggggcc cctggtggaa cagggccgcg     1260
tgcgggccgc cactgtgggc tccctggccg ccagccgct acaggagcgg cccaggcct      1320 ggggcgagcg gctgcgcgcg cggatggagg agatgggcag ccggacccgc gaccgcctgg     1380
acgaggtgaa ggagcaggtg gcggaggtgc gcgccaagct ggaggagcag gcccagcaga     1440
tacgcctgca ggccgaggcc ttccaggccc gcctcaagag ctggttcgag ccctggtgg      1500 aagacatgca gcgccagtgg gccgggctgg tggagaaggt gcaggctgcc gtgggcacca     1560
gcgccgcccc tgtgcccagc gacaatcact gaacgccgaa gcctgcagcc atgcgacccc     1620
acgccacccc gtgcctcctg cctccgcgca gcctgcagcg ggagaccctg tccccgcccc     1680
agccgtcctc ctggggtgga ccctagttta ataaagattc accaagtttc acgcaaaaaa     1740
aaaa                                                                 1744

<210> SEQ ID NO 2
<211> LENGTH: 1496
<212> TYPE: DNA
<213> ORGANISM: Mus musculus

<400> SEQUENCE: 2
gctcagaccc tggaggctaa ggacttgttt cggaaggagc tgctggccaa tcacaattgc       60
gaagatgaag gctctgtggg ccgtgctgtt ggtcacattg ctgacaggat gcctagccga      120
gggagagccg gaggtgacag atcagctcga gtggcaaagc aaccaaccct gggagcaggc      180
cctgaaccgc ttctgggatt acctgcgctg ggtgcagacg ctgtctgacc aggtccagga      240
agagctgcag agctcccaag tcacacaaga actgacgtga gtgtccagct ctttcaccct      300
cggcaggcac cagctgatcc agggttgcct cctatctggg tccccagccc cttcttgttt      360
cctttctcaa ttagtgtgta gcccaggttg gccttgaatc ctcctgcctt ctttagcctt      420
ctggatgctg ggaggaacag acatttatta cttgcttggt cgattggctt ttggcttctt      480
gagacaggat cccattctgt aactcaagct ggcttgaag gctctgcaat tcttatgccg      540
cagcttctca acttctggga acacaagcga gtaccatcac ctcttgcctc tgtggtttct      600
ggccccttct gtcctgcctt catctccttc ctgtgtttcc tctggcctg cagggcactg      660 atggaggaca ctatgacgga agtaaaggct tacaaaaagg agctggagga acagctgggt      720
```

| | |
|---|---|
| ccagtggcgg aggagacacg ggccaggctg ggcaaagagg tgcaggcggc acaggcccga | 780 |
| ctcggagccg acatggagga tctacgcaac cgactcgggc agtaccgcaa cgaggtgcac | 840 |
| accatgctgg gccagagcac agaggagata cgggcgcggc tctccacaca cctgcgcaag | 900 |
| atgcgcaagc gcttgatgcg ggatgccgag gatctgcaga agcgcctagc tgtgtacaag | 960 |
| gcagggcac gcgagggcgc cgagcgcggt gtgagtgcca tccgtgagcg cctgggcct | 1020 |
| ctggtggagc aaggtcgcca gcgcactgcc aacctaggcg ctggggccgc ccagcctctg | 1080 |
| cgcgatcgcg cccaggcttt tggtgaccgc atccgagggc ggctggagga agtgggcaac | 1140 |
| caggcccgtg accgcctaga ggaggtgcgt gagcacatgg aggaggtgcg ctccaagatg | 1200 |
| gaggaacaga cccagcaaat acgcctgcag gcggagatct tccaggcccg cctcaagggc | 1260 |
| tggttcgagc aatagtgga agacatgcat cgccagtggg caaacctgat ggagaagata | 1320 |
| caggcctctg tggctaccaa ccccatcatc accccagtgg cccaggagaa tcaatgagta | 1380 |
| tccttctcct gtcctgcaac aacatccata tccagccagg tggccctgtc tcaagcacct | 1440 |
| ctctggccct ctggtggccc ttgcttaata aagattctcc gagcacaaaa aaaaaa | 1496 |

```
<210> SEQ ID NO 3
<211> LENGTH: 680
<212> TYPE: DNA
<213> ORGANISM: Homo sapiens

<400> SEQUENCE: 3
```

| | |
|---|---|
| gagcaggtgc aggaggagct gctcagctcc caggtcaccc aggaactgag gtgagtgtcc | 60 |
| ccatcctggc ccttgaccct cctggtgggc ggctatacct ccccaggtcc aggtttcatt | 120 |
| ctgcccctgt cgctaagtct tgggggggcct gggtctctgc tggttctagc ttcctcttcc | 180 |
| catttctgac tcctggcttt agctctctgg aattctctct ctcagctttg tctctctctc | 240 |
| ttcccttctg actcagtctc tcacactcgt cctggctctg tctctgtcct tccctagctc | 300 |
| ttttatatag agacagagag atggggtctc actgtgttgc ccaggctggt cttgaacttc | 360 |
| tgggctcaag cgatcctccc gcctcggcct cccaaagtgc tgggattaga ggcatgagcc | 420 |
| accttgcccg gcctcctagc tccttcttcg tctctgcctc tgccctctgc atctgctctc | 480 |
| tgcatctgtc tctgtctcct tctctcggcc tctgccccgt tccttctctc cctcttgggt | 540 |
| ctctctggct catcccatc tcgcccgccc catcccagcc cttctccccg cctcccactg | 600 |
| tgcgacaccc tcccgccctc tcggccgcag ggcgctgatg gacgagacca tgaaggagtt | 660 |
| gaaggcctac aaatcggaac | 680 |

```
<210> SEQ ID NO 4
<211> LENGTH: 780
<212> TYPE: DNA
<213> ORGANISM: Homo sapiens

<400> SEQUENCE: 4
```

| | |
|---|---|
| tggcactggg tcgcttttgg gattacctgc gctgggtgca gacactgtct gagcaggtgc | 60 |
| aggaggagct gctcagctcc caggtcaccc aggaactgag gtgagtgtcc ccatcctggc | 120 |
| ccttgaccct cctggtgggc ggctatacct ccccaggtcc aggtttcatt ctgcccctgt | 180 |
| cgctaagtct tgggggggcct gggtctctgc tggttctagc ttcctcttcc catttctgac | 240 |
| tcctggcttt agctctctgg aattctctct ctcagctttg tctctctctc ttcccttctg | 300 |
| actcagtctc tcacactcgt cctggctctg tctctgtcct tccctagctc ttttatatag | 360 |
| agacagagag atggggtctc actgtgttgc ccaggctggt cttgaacttc tgggctcaag | 420 |

```
cgatcctccc gcctcggcct cccaaagtgc tgggattaga ggcatgagcc accttgcccg    480
gcctcctagc tccttcttcg tctctgcctc tgccctctgc atctgctctc tgcatctgtc    540
tctgtctcct tctctcggcc tctgccccgt tccttctctc cctcttgggt ctctctggct    600
catccccatc tcgcccgccc catcccagcc cttctccccg cctcccactg tgcgacaccc    660
tcccgccctc tcggccgcag ggcgctgatg gacgagacca tgaaggagtt gaaggcctac    720
aaatcggaac tggaggaaca actgaccccg gtggcggagg agacgcgggc acggctgtcc    780
```

<210> SEQ ID NO 5
<211> LENGTH: 19
<212> TYPE: DNA
<213> ORGANISM: prArtificial Sequence
<220> FEATURE:
<223> OTHER INFORMATION: primer

<400> SEQUENCE: 5
cagcggaggt gaaggacgt                                                  19

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
agaggccgag agaaggagac                                                 20

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
ttgttcctcc agttccgatt tgta                                            24

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gctcagaccc tggaggctaa                                                 20

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
tgggctacac actaattgag aaa                                             23

<210> SEQ ID NO 10
<211> LENGTH: 24
<212> TYPE: DNA
<213> ORGANISM: Artificial Sequence
<220> FEATURE:

<223> OTHER INFORMATION: primer

<400> SEQUENCE: 10
ctgttcctcc agctcctttt tgta                                    24

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
tgccgcagct tctcaacttc tgggaac                                 27

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
tgggctacac actaattgag aaa                                     23

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ggctggtctt gaacttctgg                                         20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
agaggccgag agaaggagac                                         20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gcgttgctgg tcacattcct                                         20

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
agggtcaagg gccaggatg                                          19

```
<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
cccaggtcac ccaggaact                                                    19

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
tccgatttgt aggccttcaa ct                                                22

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
aacagcgaca cccatcctc                                                    19

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
cataccagga aatgagcttg acaa                                              24
```

US 7,771,967 B2

NUCLEIC ACID ENCODING APOLIPOPROTEIN E-I3

CROSS-REFERENCE

This application claims the benefit of U.S. Provisional Patent Application No. 60/876,937, filed Dec. 22, 2006, which application is incorporated herein by reference in its entirety.

BACKGROUND

Apolipoprotein E (apoE), a 34,000 molecular weight protein, is the product of a single gene on chromosome 19 and exists in three major isoforms designated apoE2, apoE3 and apoE4. ApoE mRNA is abundant in the brain, where it is synthesized and secreted primarily by astrocytes. Although apoE is synthesized in the brain primarily by astrocytes, neurons in the central nervous system (CNS) express apoE in response to excitotoxic stress and other insults. It has been shown that neuronal expression of apoE, especially apoE4, contributes to the pathogenesis of Alzheimer's Disease (AD), such as neurofibrillary tangle formation and mitochondrial dysfunction. However, the molecular mechanisms underlying the regulation of neuronal expression of apoE are poorly understood.

There are currently no effective therapies for arresting (and, more importantly, reversing) the impairment of central and peripheral nervous system function once an irreversible degenerative cascade begins. Likewise, there is no current therapy for restoration of normal, central and peripheral nervous system function when the induced stress has a less catastrophic or partially reversible effect compared to the dementias. There is a need in the art for effective therapies for treating disorders associated with apoE.

Literature

Huang (2006) *Curr. Opinion Drug Discovery Devel.* 9:627-641; Xu et al. (2006) *J. Neurosci.* 26:4985-4994; Mahley et al. (2006) *Proc. Natl. Acad. Sci. USA* 103:5644-5651; Huang (2006) *Neurology* 66:S79-S85; Chou et al. (2005) *Biophys. J.* 88:455-466; Weisgraber ((1994) *Adv. Protein Chem.* 45:249-302.

SUMMARY OF THE INVENTION

The present invention provides nucleic acids comprising a nucleotide sequence encoding an apolipoprotein E (apoE) mRNA splice variant, e.g., an unprocessed apoE, that retains intron 3; and vectors and host cells comprising same. The present invention further provides screening methods to identify agents that inhibit cleavage of intron-3 from the apoE splice variant. The present invention further provides methods of treating apoE-related neurological disorders, involving administering an agent that inhibits removal of intron-3 from a precursor apoE mRNA.

BRIEF DESCRIPTION OF THE DRAWINGS

FIGS. 2A-2F depict neuron-specific expression of apoE-I3.

FIGS. 4A-D depict control of apoE expression in neurons by apoE-I3 retention/splicing.

FIG. 10A depicts a nucleotide sequence of a human apoE-I3 transcript. FIG. 10B depicts a nucleotide sequence of a mouse apoE-I3 transcript. FIGS. 10C and 10D depict further exemplary nucleic acids. FIG. 10C depicts a human apoE intron-3 sequence (underlined), plus 50 nucleotides (nt) 5' and 50 nt 3'. FIG. 10D depicts a human apoE intron-3 sequence (underlined), plus 100 nt 5' and 100 nt 3'.

DEFINITIONS

Figure 1A:
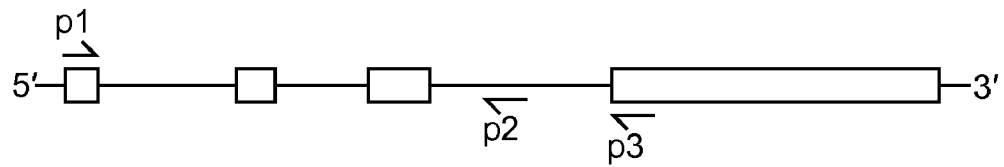
FIGS. 1A-C depict an apoE transcript, designated apoE-I3, that retains intron-3.

As used herein, an "apoE-associated disorder" or an "apoE-related disorder" is any disorder that is caused by the presence of apoE (e.g., apoE3 or apoE4) in a cell, in the serum, in the interstitial fluid, in the cerebrospinal fluid, or in any other bodily fluid of an individual; any disorder that is characterized by the presence of apoE3 or apoE4; a symptom of a disorder that is caused by the presence of apoE3 or apoE4 in a cell or in a bodily fluid; a phenomenon associated with a disorder caused by the presence in a cell or in a bodily fluid of apoE3 or apoE4; and the sequelae of any disorder that is caused by the presence of apoE3 or apoE4. ApoE-associated disorders include apoE-associated neurological disorders and disorders related to high serum lipid levels. ApoE-associated neurological disorders include, but are not limited to, sporadic Alzheimer's disease; familial Alzheimer's disease; poor outcome following a stroke; poor outcome following traumatic head injury; and cerebral ischemia. Phenomena associated with apoE-associated neurological disorders include, but are not limited to, neurofibrillary tangles; amyloid deposits; memory loss; and a reduction in cognitive function. ApoE-related disorders associated with high serum lipid levels include, but are not limited to, atherosclerosis, and coronary artery disease. Phenomena associated with such apoE-associated disorders include high serum cholesterol levels.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, humans; and non-human mammals, e.g., murines, simians, mammalian farm animals, mammalian sport animals, and mammalian pets.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells. An isolated polynucleotide can be purified, e.g., at least 85% pure, at least 90% pure, at least 95% pure, or at least 98% pure.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems.

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

"Operably linked" refers to a juxtaposition wherein the components so described are in a relationship permitting them to function in their intended manner. For instance, a promoter is operably linked to a coding sequence if the promoter affects its transcription or expression.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid, and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector.

As used herein, the term "neurons" or "neuronal cells" includes any cell population that includes neurons of any type, including, but not limited to, primary cultures of brain cells that contain neurons, isolated cell cultures comprising primary neuronal cells, neuronal precursor cells, tissue culture cells that are used as models of neurons, and mixtures thereof.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an apolipoprotein E precursor transcript" includes a plurality of such transcripts and reference to "the agent that inhibits removal of intron-3" includes reference to one or more such agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides nucleic acids comprising a nucleotide sequence encoding an apolipoprotein E (apoE) mRNA splice variant, designated apoE-I3, which retains intron 3; and vectors and host cells comprising same. The present invention further provides screening methods to identify agents that inhibit cleavage of intron-3 from the apoE splice variant. The present invention further provides methods of treating apoE-related neurological disorders, involving administering an agent that inhibits removal of intron-3 from a precursor apoE mRNA (e.g., apoE-I3 or other apoE precursor mRNA, e.g., apoE precursor mRNA retaining intron-3).

ApoE-I3 was detected in neuronal cells and primary neurons but not astrocytic cells and primary astrocytes from human or mice by reverse transcriptase polymerase chain reaction (RT-PCR). ApoE-I3 mRNA was found predominantly in cortical and hippocampal neurons in both wildtype and human apoE knock-in mice, as detected by in situ hybridization. Cell fractionation and real time RT-PCR revealed that over 99% of the apoE-I3 mRNA was retained in nuclei without protein translation. In transfected neuronal cells and primary neurons, apoE expression was dramatically increased, when intron 3 was deleted from a genomic DNA construct, and markedly decreased, when intron 3 was added into a cDNA construct, suggesting that intron-3 retention negatively regulates apoE expression in neurons. Moreover, the up-regulation of apoE expression by astrocyte-conditioned medium was abolished in the absence of intron 3, suggesting that astroglial regulation of neuronal apoE expression acts through the processing of apoE-I3. In mouse brains, in response to excitotoxic challenge, the apoE-I3 mRNA signal was markedly increased in normal hippocampal and cortical neurons but diminished in degenerating neurons. In contrast, apoE mRNA appeared in degenerating, but not normal, neurons. These data suggest a precursor-product relationship between apoE-I3 and apoE mRNA, which was supported by a pause-chase transcriptional inhibition study. Thus, neuronal expression of apoE is likely controlled by transcriptional regulation of apoE-I3 under normal conditions and by processing of apoE-I3 into mature apoE mRNA in response to neuronal injury.

Nucleic Acids

The present invention provides nucleic acids ("polynucleotides") comprising a nucleotide sequence encoding an apolipoprotein E (apoE) mRNA splice variant, designated apoE-I3, which retains intron 3; and vectors and host cells comprising same. A subject apoE-I3 polynucleotide is in some embodiments isolated. A subject apoE-I3 polynucleotide is in some embodiments recombinant, or synthetic. A subject apoE-I3 polynucleotide is useful in screening methods for identifying agents that inhibit or reduce removal of intro-3 from an apoE-I3 mRNA transcript.

In some embodiments, a subject apoE-I3 polynucleotide comprises a nucleotide sequence having at least about 75%, at least about 80%, at least about 85%, at least about 90%, at least about 95%, at least about 98%, at least about 99%, or more, nucleotide sequence identity with the nucleotide sequence set forth in FIG. 10A (SEQ ID NO:1) or FIG. 10B (SEQ ID NO:2).

A subject apoE-I3 polynucleotide comprises at least intron-3 (e.g., a nucleotide sequence having at least about 75%, at least about 80%, at least about 85%, at least about 90%, at least about 95%, at least about 98%, at least about 99%, or more, nucleotide sequence identity with nucleotides 295-874 of SEQ ID NO:1; or a nucleotide sequence having at least about 75%, at least about 80%, at least about 85%, at least about 90%, at least about 95%, at least about 98%, at least about 99%, or more, nucleotide sequence identity with nucleotides 277-653 of SEQ ID NO:2); and from about 25 nt to about 5000 nt (or more) 5' and/or 3' of the intron-3 nucleotide sequence. For example, in some embodiments, a subject apoE-I3 polynucleotide comprises at least intron-3, as described above, and from about 25 nt to about 50 nt, from about 50 nt to about 100 nt, from about 100 nt to about 200 nt, from about 200 nt to about 500 nt, from about 500 nt to about 1000 nt, from about 1000 nt to about 2000 nt, from about 2000 nt to about 3000 nt, from about 3000 nt to about 4000 nt, or from about 4000 nt to about 5000 nt, or more, 5' and/or 3' of the intron-3 sequence.

In some embodiments, a subject apoE-I3 polynucleotide comprises a nucleotide sequence having at least about 75%, at least about 80%, at least about 85%, at least about 90%, at least about 95%, at least about 98%, at least about 99%, or more, nucleotide sequence identity with a contiguous stretch of from about 700 nucleotides (nt) to about 750 nt, from about 750 nt to about 800 nt, from about 800 nt to about 900 nt, from about 900 nt to about 1000 nt, from about 1000 nt to about 1100 nt, from about 1100 nt to about 1200 nt, from about 1200 nt to about 1300 nt, from about 1300 nt to about 1400 nt, from about 1400 nt to about 1500 nt, from about 1500 nt to about 1600 nt, from about 1600 nt to about 1700 nt, or from about 1700 nt to about 1740 nt of the nucleotide sequence set forth in SEQ ID NO:1, wherein the apo-I3 polynucleotide comprises at least a nucleotide sequence having about at least about 75%, at least about 80%, at least about 85%, at least about 90%, at least about 95%, at least about 98%, at least about 99%, or more, nucleotide sequence identity with nucleotides 295-874 of SEQ ID NO: 1. For example, in some embodiments, a subject apoE-I3 polynucleotide comprises a nucleotide sequence having at least about 75%, at least about 80%, at least about 85%, at least about 90%, at least about 95%, at least about 98%, at least about 99%, or more, nucleotide sequence identity with the nucleotide sequence set forth in SEQ ID NO:3 (intron-3 plus 50 nt 5' and 50 nt 3' flanking sequences) or with the nucleotide sequence set forth in SEQ ID NO:4 (intron-3 plus 100 nt 5' and 100 nt 3' flanking sequences).

The sequence flanking the intron-3 sequence will in some embodiments encode an apolipoprotein-E. In some embodiments, the nucleotide sequences flanking the intron-3 sequence encode an apoE polypeptide or a fragment of an apoE polypeptide. ApoE polypeptides include, but are not limited to, apoE3 and apoE4. ApoE polypeptides are known in the art, as are nucleotide sequences encoding same. See, e.g., Weisgraber ((1994) *Adv. Protein Chem.* 45:249-302, for the disclosure of amino acid sequences of apoE from a variety of species; e.g., see FIG. 1 on page 252 of Weisgraber, which FIG. 1 provides amino acid sequences of apoE from a variety of species. See, e.g., GenBank Accession No. NP_000032, human apoE4; GenBank Accession No. AAB59518, human apoE; GenBank Accession No. P05770, baboon apoE; GenBank Accession No. P10517, cynomolgous monkey apoE; GenBank Accession No. NP_620183, rat apoE; GenBank Accession No. NP_033826, mouse apoE; GenBank Accession No. P23529, guinea pig apoE; GenBank Accession No. P18287, rabbit apoE; GenBank Accession No. NP_776416 cow apoE; GenBank Accession No. P18649, dog apoE; GenBank Accession No. Q7M2U7, sea lion apoE.

Nucleotide sequences encoding such apoE polypeptides are known in the art. See, e.g., GenBank Accession No. NM_000041 (human apoE); GenBank Accession No. NM_138828 (rat apoE); NM_009696 (mouse apoE). In some embodiments, a nucleotide sequence flanking the intron-3 sequence has at least about 75%, at least about 80%, at least about 85%, at least about 90%, at least about 95%, at least about 98%, or greater than 98%, nucleotide sequence identity to a contiguous stretch of from 50 nt to 100 nt, from 100 nt to 500 nt, from 500 nt to 1000 nt, or more than 1000 nt of a nucleotide sequence encoding a human apoE, a mouse apoE, a rat apoE, or other known apoE.

In some embodiments, a subject apoE-I3 polynucleotide is an mRNA. In other embodiments, a subject apoE-I3 polynucleotide is a cDNA. In other embodiments, a subject apoE-I3 polynucleotide is a DNA. In other embodiments, a subject apoE-I3 polynucleotide is present in an expression vector or other recombinant construct.

In some embodiments, a subject apoE-I3 nucleic acid comprises an apoE-I3 nucleotide sequence that encodes a fusion protein, e.g., a protein that comprises an apolipoprotein E fused to a heterologous protein (a "fusion partner"), e.g., a protein other than an apoE protein. Suitable fusion partners include, e.g., epitope tags; proteins that provide for a detectable signal; proteins that provide for solubility; proteins that provide for insertion into a membrane; proteins that provide for ease of purification of the fusion protein, e.g., a poly (histidine) tag (e.g., His$_6$), a glutathione-S-transferase tag, and the like.

In some embodiments, a subject apoE-I3 nucleic acid comprises an apoE-I3 nucleotide sequence is operably linked to a nucleotide sequence encoding a reporter polypeptide. Suitable reporter polypeptides include, but are not limited to, epitope tags (e.g., hemagglutinin, FLAG, etc.); fluorescent polypeptides; and enzymes that act on a substrate to yield a detectable product, such as a colored product, a fluorescent product, a luminescent product, etc., where suitable enzymes include, e.g., β-galactosidase, luciferase, horse radish peroxidase, alkaline phosphatase, etc.

Suitable fluorescent polypeptides include, but are not limited to, green fluorescent protein (GFP; Chalfie, et al., *Science* 263(5148):802-805 (Feb. 11, 1994); and enhanced GFP (EGFP); Clontech-Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12):5408-5417 (1993)), β-galactosidase (Nolan, et al., Proc Natl Acad Sci USA 85(8):2603-2607 (April 1988)) and *Renilla* WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558), a GFP from species such as *Renilla reniformis, Renilla mullei*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; U.S. Patent Publication No. 2002/0197676, or U.S. Patent Publication No. 2005/0032085; and the like.

Recombinant Constructs

In some embodiments, a subject apoE-I3 polynucleotide is contained within a recombinant vector, e.g., a recombinant nucleic acid that provides for amplification and/or expression of the apoE-I3 polynucleotide. The present invention thus provides apoE-I3 recombinant constructs comprising a subject apoE-I3 polynucleotide.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli* and yeast). Thus, for example, a nucleic acid encoding a mevalonate pathway gene product(s) is included in any one of a variety of expression vectors for expressing the mevalonate pathway gene product(s). Such vectors include chromosomal, nonchromosomal and synthetic DNA sequences.

Numerous suitable expression vectors are known to those of skill in the art, and many are commercially available. The following vectors are non-limiting examples of expression vectors suitable for use in bacterial host cells: T7 expression vectors (e.g., pET28; Novegen, Madison, Wis.), pQE vectors (Qiagen), pBluescript plasmids, pNH vectors, lambda-ZAP vectors (Stratagene); pTrc99a, pKK223-3, pDR540, and pRIT2T (Pharmacia). The following vectors are non-limiting examples of expression vectors suitable for use in eukaryotic host cells: pcDNA, pXT1, pSG5 (Stratagene), pSVK3, pBPV, pMSG, and pSVLSV40 (Pharmacia). However, any other plasmid or other vector may be used so long as it is compatible with the host cell.

Integrative vectors can be conditionally replicative or suicide plasmids, bacteriophages, transposons or linear DNA fragments obtained by restriction hydrolysis or polymerase chain reaction (PCR) amplification. Selection of the recombination event can be accomplished by means of selectable genetic marker such as genes conferring resistance to antibiotics (for instance kanamycin, erythromycin, chloramphenicol, or gentamycin), genes conferring resistance to heavy metals and/or toxic compounds or genes complementing auxotrophic mutations (for instance pur, leu, met, aro). Suitable selectable markers for eukaryotic cells include, but are not limited to, dihydrofolate reductase and neomycin resistance.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some embodiments, a subject apoE-I3 nucleotide sequence is operably linked to a promoter, where the promoter is one that is functional in a prokaryotic host cell. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction.* Macmillan, London, UK, Vol. 10, pp. 143-162); an SP6 promoter (see, e.g., Melton et al. (1984) *Nucl. Acids Res.* 12:7035-7056); and the like.

In some embodiments, a subject apoE-I3 nucleotide sequence is operably linked to a promoter, where the promoter is one that is functional in a eukaryotic host cell. Non-limiting examples of suitable eukaryotic promoters include CMV immediate early, HSV thymidine kinase, early and late SV40, long terminal repeats (LTRs) from retrovirus, and mouse metallothionein-I. In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, and the like. Selection of the appropriate vector and promoter is well within the level of ordinary skill in the art. The expression vector may also contain a ribosome binding site for translation initiation and a transcription terminator. The expression vector may also include appropriate sequences for amplifying expression.

In some embodiments, the promoter is an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., C1857-repressed lambda-based expression vectors; see, e.g., Hoffmann et al. (1999) *FEMS Microbiol Lett.* 177(2):327-34); and the like.

In some embodiments, the promoter is a constitutive promoter. Suitable constitutive promoters for use in prokaryotic cells are known in the art and include, but are not limited to, a sigma70 promoter, e.g., a consensus sigma70 promoter.

In some embodiments, the control sequence is a neuron-specific control sequence. Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; and a CMV enhancer/platelet-derived growth factor-β promoter (see, e.g., Liu et al. (2004) *Gene Therapy* 11:52-60).

In eukaryotic cells, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathem et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the chromosome.

In addition, the expression vector will in some embodiments contain one or more selectable marker genes to provide a phenotypic trait for selection of transformed host cells such as antibiotic resistance (e.g., tetracycline resistance, kanamycin resistance, or ampicillin resistance) in prokaryotic host cells.

Genetically Modified Host Cells

The present invention provides genetically modified host cells, e.g., isolated host cells that are genetically modified with a subject apoE-I3 polynucleotide or a subject apoE-I3 recombinant construct.

To generate a subject genetically modified host cell, one or more nucleic acids comprising nucleotide sequences encoding one or more meningococcal antigens is introduced stably or transiently into a host cell, using established techniques, including, but not limited to, electroporation, calcium phosphate precipitation, DEAE-dextran mediated transfection, liposome-mediated transfection, conjugation, transformation, and the like.

In some embodiment, the genetically modified cell is a mammalian cell line. Suitable mammalian cell lines that can be genetically modified with a subject apoE-I3 polynucleotide include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, MDCK cells (ATCC CCL-34); WI38 (ATCC CCL-75), and the like.

In some embodiments, the genetically modified cell is a neuronal cell or a neuronal-like cell. Suitable cells that can be genetically modified with a subject apoE-I3 polynucleotide include, but are not limited to, primary neuronal cells, neuronal stem cells, and immortalized neuronal cell lines. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FL (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538). In some embodiments, the cell is an astrocyte.

Screening Methods

The present invention further provides screening methods to identify agents that inhibit cleavage of intron-3 from the apoE splice variant. An apoE splice variant that retains intron-3 is referred to as an "unprocessed apoE transcript," an "unprocessed apoE nucleic acid," a "precursor apoE transcript," or a "precursor apoE nucleic acid"; and a processed apoE transcript from which the intron-3 has been removed or excised is referred to as a "processed apoE transcript" or a "processed apoE nucleic acid." The processed apoE nucleic acid is generated upon removal of intron-3 from the unprocessed apoE nucleic acid.

In some embodiments, a subject screening method is a cell-based, in vitro method. In general, the methods involve: a) contacting a test cell with a test agent and an inducing agent, where the test cell comprises an unprocessed apoE nucleic acid comprising intron-3, and where the inducing agent induces removal of intron-3 from the unprocessed nucleic acid to generate a processed apoE nucleic acid lacking intron-3; and b) determining the effect, if any, of the test agent on the level of the unprocessed apoE nucleic acid relative to the level of processed apoE nucleic acid, compared to the level of unprocessed apoE nucleic acid relative to the level of processed apoE nucleic acid in a control cell contacted with the inducing agent and not contacted with the test agent. Determining the effect of the test agent on the level of processed apoE nucleic acid can be carried out by determining: 1) the level of processed apoE nucleic acid and/or the level of a polypeptide encoded by the processed apoE nucleic acid; 2) the level of unprocessed apoE nucleic acid; 3) the level of processed apoE nucleic acid and the level of unprocessed apoE nucleic acid; or 4) the level of apoE polypeptide encoded by the processed apoE nucleic acid and the level of unprocessed apoE nucleic acid.

A test agent of interest is a test agent that reduces the level of processed apoE transcript in the test cell by at least about 10%, at least about 20%, at least about 30%, at least about 40%, at least about 50%, at least about 60%, at least about 70%, at least about 80%, or at least about 90%, or more, compared to the level of the processed apoE transcript in the absence of the test agent and in the presence of an agent that induces removal of intron-3 from an apoE-I3 nucleic acid. A test agent of interest is considered a candidate agent for the treatment of an apoE-related disorder.

In some embodiments, a test agent of interest is one that increases the level of unprocessed apoE nucleic acid in the test cell by at least about 10%, at least about 20%, at least about 30%, at least about 40%, at least about 50%, at least about 60%, at least about 70%, at least about 80%, at least about 90%, at least about 2-fold, at least about 2.-fold, at least about 3-fold, at least about 4-fold, at least about 5-fold, at least about 6-fold, at least about 10-fold, at least about 15-fold, or at least about 20-fold, or more, compared to the level of the unprocessed apoE in the absence of the test agent and in the presence of an agent that induces removal of intron-3 from an apoE-I3 nucleic acid. A test agent of interest is considered a candidate agent for the treatment of an apoE-related disorder.

In some embodiments, a test agent of interest is one that increases the ratio of unprocessed apoE nucleic acid to processed apoE nucleic acid in a test cell, compared to the ratio of unprocessed apoE nucleic acid to processed apoE nucleic acid in a control cell. For example, in some embodiments, a test agent of interest is one that increases the ratio of unprocessed apoE nucleic acid to processed apoE nucleic acid in a test cell to from about 1:1 to about 1.25:1, from about 1.25:1 to about 1.5:1, from about 1.5:1 to about 2:1, from about 2:1 to about 2.5:1, from about 2.5:1 to about 3:1, from about 3:1 to about 5:1, from about 5:1 to about 7.5:1, from about 7.5:1 to about 10:1, or greater than 10:1.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with other macromolecules such as proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a test cell (e.g., a test cell cultured in the absence of the test agent; a test cell cultured in the absence of the test agent and in the presence of an inducing agent). Generally a plurality of assay mixtures is run in parallel with different test agent concentrations to obtain a differential response to the various concentrations. Typically, one of these concentrations serves as a negative control, i.e. at zero concentration or below the level of detection.

Agents that induce removal of intron-3 from an unprocessed apoE transcript (e.g., from an apoE-I3 nucleic acid) include, but are not limited to, an excitotoxic signal; an astrocyte-derived factor(s); and the like. An astrocyte-derived factor can be provided as astrocyte-conditioned medium, e.g., culture medium in which astrocytes are grown in vitro for a suitable period of time, e.g., 2-4 hours, 4-8 hours, 8-12 hours, 12-18 hours, 18-24 hours, or longer. Astrocytes include primary astrocytes, and astrocyte cell lines (e.g., U87, a human astrocyte cell line; and C6, a mouse astrocyte cell line).

In some embodiments, a test cell is a neuronal cell line (e.g., Neuro-2A, NT2, and the like) that is genetically modified with an unprocessed apoE nucleic acid (e.g., an apoE-I3 nucleic acid). The effect, if any, of the test agent on the level of the processed apoE nucleic acid is determined using any of a number of methods.

A number of methods are available for analyzing nucleic acids for the presence and/or level of a specific mRNA in a cell. The mRNA may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2-14.33. Alternatively, various methods are known in the art that utilize oligonucleotide ligation as a means of detecting polymorphisms, for examples see Riley et al. (1990), *Nucl. Acids Res.* 18:2887-2890; and Delahunty et al. (1996), *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

A variety of different methods for determining the nucleic acid abundance in a sample are known to those of skill in the art, where particular methods of interest include those described in: Pietu et al., Genome Res. (June 1996) δ: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

For example, the level of unprocessed apoE nucleic acid can be detected using oligonucleotide primers that, in the presence of a DNA polymerase, prime synthesis of a nucleic acid comprising an intron-3 nucleotide sequence. The level of processed apoE nucleic acid can be detected using oligonucleotide primers that prime synthesis of a nucleic acid comprising apoE nucleotide sequences that lack intron-3, e.g., apoE nucleotide sequences that flank intron-3 in the unprocessed apoE nucleic acid and that are juxtaposed or adjacent one another in the processed apoE nucleic acid.

In other embodiments, an apoE polypeptide encoded by the processed nucleic acid is detected. For example, an immunological assay is used to detect the apoE polypeptide. Antibody specific for the apoE polypeptide is added to the cell sample, and incubated for a period of time sufficient to allow binding to an epitope on the apoE polypeptide, e.g., at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. Alternatively, the secondary antibody conjugated to a fluorescent compound, e.g. fluorescein, rhodamine, Texas red, etc. The absence or presence of antibody binding may be determined by various methods, including flow cytometry of dissociated cells, microscopy, radiography, scintillation counting, an enzyme-linked immunosorbent assay, a protein blot assay, etc.

In other embodiments, the processed nucleic acid encodes an apoE fusion polypeptide, comprising an apoE polypeptide and a fusion partner, where the fusion partner provides a detectable signal. Suitable fusion partners include, but are not limited to, a fluorescent protein, a chromogenic protein, an enzyme that yields a product that produces a detectable signal, etc. Suitable enzymes include, but are not limited to, β-galactosidase, horse radish peroxidase, luciferase, and alkaline phosphatase.

Suitable fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis*, *Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like. Where the fusion partner is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc.

In some embodiments, a subject cell-based in vitro screening method comprises a) contacting a test cell with a test agent and an inducing agent, where the test cell is genetically modified with a nucleic acid that comprises an unprocessed apoE nucleic acid comprising intron-3, wherein the unprocessed apoE-I3 nucleic acid is operably linked to a nucleotide sequence encoding a reporter polypeptide, and where the inducing agent induces removal of intron-3 from the unprocessed nucleic acid to generate a processed apoE nucleic acid lacking intron-3, wherein the processed apoE nucleic acid is operably linked to a nucleotide sequence encoding a reporter polypeptide, and wherein the encoded apoE-reporter polypeptide is produced in the cell; and b) determining the effect, if any, of the test agent on the level of encoded apoE-reporter polypeptide relative to the level of apoE-reporter polypeptide in a control cell contacted with the inducing agent and not contacted with the test agent. In some embodiments, the inducing agent is astrocyte conditioned medium. In some embodiments, the reporter polypeptide is a fluorescent protein.

Evaluation in vivo

A candidate agent can be further evaluated, in a secondary screen, for efficacy in vivo, using an animal model of an apoE-related disorder. Such secondary screens can employ any phenomena associated learning impairment, dementia or cognitive disorders that can be readily assessed in an animal model. The screening can include assessment of phenomena including, but not limited to: 1) analysis of molecular markers (e.g., levels of apoE mRNA and/or protein in brain tissue; and formation of neurite plaques); 2) assessment behavioral symptoms associated with memory and learning; 3) detection of neurodegeneration characterized by progressive and irreversible deafferentation of the limbic system, association neocortex, and basal forebrain (neurodegeneration can be measured by, for example, detection of synaptophysin expression in brain tissue) (see, e.g., Games et al. *Nature* 373:523-7 (1995)). These phenomena may be assessed in the screening assays either singly or in any combination.

Generally, the screen will include control values (e.g., the extent of neuronal and/or behavioral deficits in the test animal in the absence of test compound(s)). Test substances which are considered positive, i.e., likely to be beneficial in the treatment of apoE-mediated disorders, will be those which have a substantial effect upon neuronal and behavioral deficits, formation of neurofibrillary tangles, Aβ levels, and associated disorders.

Methods for assessing these phenomena, and the effects expected of a candidate agent for treatment of apoE-associated disorders, are known in the art. For example, methods for using transgenic animals in various screening assays for, for example, testing compounds for an effect on Alzheimer's disease (AD), are found in WO 9640896, published Dec. 19, 1996; WO 9640895, published Dec. 19, 1996; WO 9511994, published May 4, 1995 (describing methods and compositions for in vivo monitoring of Aβ; each of which is incorporated herein by reference with respect to disclosure of methods and compositions for such screening assays and techniques). Examples of assessment of these phenomena are provided below, but are not meant to be limiting.

Pathological Studies

After exposure to the candidate agent, the animals are sacrificed and analyzed by immunohistology for, e.g.: 1) levels of neurofibrillary tangles (NFTs) in the brain and/or 2) levels of Aβ in the brain and/or 3) neuronal loss and/or 4) other neuropathologies. The brain tissue is fixed (e.g, in 4% paraformaldehyde) and sectioned; the sections are stained with antibodies reactive with Aβ, and/or p-tau, and/or p-NF-H. Secondary antibodies conjugated with fluorescein, rhodamine, horse radish peroxidase, or alkaline phosphatase are used to detect the primary antibody. These experiments permit identification of neurofibrillary tangles and Aβ deposition and the regionalization of these NFTs to specific areas of the brain.

Sections can also be stained with other diagnostic antibodies recognizing antigens such as A1z-50, A2B5, neuron-specific enolase, and others that are characteristic of neurodegeneration. Staining with thioflavins and congo red can also be carried out to analyze co-localization of Aβ deposits within the neuritic plaques and NFTs.

Behavioral Studies

Behavioral tests designed to assess learning and memory deficits can be employed. An example of such as test is the Morris Water maze (Morris *Learn Motivat* 12:239-260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues. Alternatively, or in addition, memory and learning deficits can be studied using a 3 runway panel for working memory impairment (attempts to pass through two incorrect panels of the three panel-gates at four choice points) (Ohno et al. *Pharmacol Biochem Behav* 57:257-261 (1997)).

Studies of Animal Models of Neuronal Damage

Rodent models of neuronal damage, for example neuronal damage caused by cerebral ischemia, may be examined to determine the role of apoE3 and apoE4 in the extent of neuronal damage caused by traumatic events as well as their role in neuronal remodeling, repair and recovery from such insults. Rodent models of cerebral ischemia, both global ischemia and focal ischemia, are useful for studying mechanisms controlling the occurrence of cerebral ischemia and potential therapeutic strategies for treatment of injury caused by ischemic events. Animal models of global ischemia, which is usually transient, have widely affected brain areas but typically give rise to neuronal alterations in selectively vulnerable brain regions. Examples of such models include, but are not limited to, the two vessel occlusion model of forebrain ischemia, the four vessel occlusion model of forebrain ischemia, and ischemia models involving elevated cerebrospinal fluid pressure. See Ginsberg and Busto, *Stroke,* 20:1627-1642 (1989), which is herein incorporated by reference. Models of focal ischemia may mimic ischemic stroke injury, and typically give rise to localized brain infarction. Examples of models of focal ischemia include, but are not limited to, middle cerebral artery occlusion, photochemically induced focal cerebral thrombosis, blood clot embolization, microsphere embolization and the like. See McAuley, *Cerebrovasc. Brain Metab. Review,* 7:153-180 (1995) which is herein incorporated by reference.

Therapeutic Methods

The present invention further provides methods of treating an apoE-related disorder. The methods generally involve administering to an individual in need thereof an effective amount of an agent that inhibits processing of an unprocessed apoE nucleic acid (e.g., an apoE-I3 nucleic acid) to remove intron-3.

An agent that inhibits processing of an unprocessed apoE nucleic acid (e.g., an apoE-I3 nucleic acid) to remove intron-3 is referred to as a "therapeutic agent." A therapeutic agent is administered to an individual in need thereof in a formulation comprising the agent and at least one pharmaceutically acceptable excipient. Pharmaceutically acceptable excipients are known to those skilled in the art, and have been amply described in a variety of publications, including, for example, A. Gennaro (1995) "Remington: The Science and Practice of Pharmacy", 19th edition, Lippincott, Williams, & Wilkins.

An "effective amount" of a therapeutic agent means a dosage sufficient to produce a desired result, e.g., a reduction in neurofibrillary tangles, an improvement in learning, memory, a reduction in Aβ levels, a reduction in neuronal cell death, etc. A therapeutic agent that inhibits processing of an unprocessed apoE nucleic acid (e.g., an apoE-I3 nucleic acid) to remove intron-3 can be delivered in such a manner as to avoid the blood-brain barrier. A therapeutic agent can be formulated and/or modified to enable the agent to cross the blood-brain barrier.

In the subject methods, a therapeutic agent can be administered to the host using any convenient means capable of resulting in the desired reduction in symptom(s). Thus, the agent can be incorporated into a variety of formulations for therapeutic administration. More particularly, a therapeutic agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a therapeutic agent may be administered in the form of a pharmaceutically acceptable salts, or can be used alone or in appropriate association, as well as in combination, with other pharmaceutically active compounds. The following methods and excipients are merely exemplary and are in no way limiting.

For oral preparations, a therapeutic agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A therapeutic agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A therapeutic agent can be utilized in aerosol formulation to be administered via inhalation. A therapeutic agent can be formulated into pressurized acceptable propellants such as dichlorodifluoromethane, propane, nitrogen and the like.

Furthermore, a therapeutic agent can be made into suppositories by mixing with a variety of bases such as emulsifying bases or water-soluble bases. A therapeutic agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more therapeutic agents. Similarly, unit dosage forms for injection or intravenous administration may comprise the therapeutic agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a therapeutic agent calculated in an amount sufficient to produce the desired effect in association with a pharmaceutically acceptable diluent, carrier or vehicle. The specifications the unit dosage form depend on the particular agent employed and the effect to be achieved, and the pharmacodynamics associated with each agent in the host.

Other modes of administration will also find use with the subject invention. For instance, a therapeutic agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A therapeutic agent can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Routes of Administration

A therapeutic agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other enteral and parenteral routes of administration. Routes of administration may be combined, if desired, or adjusted depending upon the agent and/or the desired effect. The therapeutic agent can be administered in a single dose or in multiple doses. In some embodiments, the composition is administered orally. In other specific embodiments, the therapeutic agent is administered via an inhalational route. In some embodiments, the therapeutic agent is administered intranasally.

The therapeutic agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The therapeutic agent can also be delivered to the subject by enteral administration. Enteral routes of administration include, but are not necessarily limited to, oral and rectal (e.g., using a suppository) delivery.

Methods of administration of the therapeutic agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an apoE4-associated neurological disorder and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

Subjects Suitable for Treatment

A variety of subjects are suitable for treatment with a subject method. Suitable subjects include any individual, particularly a human, who has an apoE-associated disorder, who is at risk for developing an apoE-associated disorder, who has had an apoE-associated disorder and is at risk for recurrence of the apoE-associated disorder, or who is recovering from an apoE-associated disorder.

Such subjects include, but are not limited to, individuals who have been diagnosed as having Alzheimer's disease; individuals who have suffered one or more strokes; individuals who have suffered traumatic head injury; individuals who have high serum cholesterol levels; individuals who have Aβ deposits in brain tissue; individuals who have had one or more cardiac events; subjects undergoing cardiac surgery; subjects with Parkinson's disease; subjects with amyotrophic lateral sclerosis; and subjects with multiple sclerosis.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second (s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Intron-3 Retention Negatively Controls Neuronal Expression of Apolipoprotein E in the Central Nervous System Methods Reagents and animals. Minimum essential medium (MEM), Opti-MEM, and fetal bovine serum were from Life Technologies (Rockville, Md.). ECL was from Amersham (Arlington, Ill.). Polyclonal goat anti-human apoE antibody was from Calbiochem. Kainic acid was from Sigma (St Louis, Mo.). Wildtype mice were from the Jackson Laboratory (Bar Harbor, Me.). Human apoE3 or apoE4 knock-in mice were from Taconic (Hudson, N.Y.). All mice were weaned at 21 days of age, housed in a barrier facility at the Gladstone Animal Core with a 12-h light/12-h dark cycle, and fed a chow diet containing 4.5% fat (Ralston Purina).

Determination of the full-length cDNA of apoE-I3 by 3'- and 5'-RACE. Human and mouse brain total RNA from Ambion was used as templates in the reverse transcription (RT) reaction. For 3'-rapid amplification of cDNA ends (3'-RACE), an anchored oligo-dT primer (ordered from Invitrogen) was used as reverse transcription primer. After the RT reaction, a forward primer corresponding to a sequence within intron 3 and a backward primer corresponding to the anchor sequence of the RT primer was used to amplify the 3'-end of apoE-I3. The polymerase chain reaction (PCR) products were subcloned into a TOPO vector (Invitrogen) and sequenced. A 5'-RACE kit (Ambion) was used to detect the 5'-end of apoE-I3. Through the RNA ligation reaction, an anchored poly G sequence was added to the 5'-end of different RNAs from human or mouse brains. The RT reaction was then performed with an oligo-dT primer, and the 5'-end of apoE-I3 was amplified by a forward primer corresponding to the anchor sequence and a backward primer corresponding to a sequence within intron 3. The PCR products were then subcloned into a TOPO vector and sequenced.

Cell cultures. Neuro-2a, U87, and C6 cells (American Type Culture Collection, Manassas, Va.) were maintained at 37° C. in a humidified 5% $CO_2$ incubator in MEM containing 10% FBS supplemented with nonessential amino acids, penicillin, and streptomycin. Neuro-2a cells stably transfected with a human apoE3 or apoE4 genomic DNA were established in our laboratory and reported previously. Human neuronal precursor NT2/D1 cells were kindly provided by Dr. Virginia M.-Y. Lee (University of Pennsylvania School of Medicine, Philadelphia) and maintained in Opti-MEM-I (GIBCO) containing 5% FBS and penicillin/streptomycin. The cells were treated with retinoic acid to induce differentiation into NT2 neurons.

Primary cultures of cortical or hippocampal neurons were prepared from P1 wild type rat or mouse. As determined by immunostaining with cell-specific antibodies, >95% of cells in 6-day-old cortical cultures in vitro are positive for neuron-specific enolase. Primary astrocytes were prepared from day 1 wild type mice. As determined by immunostaining with cell-specific antibodies, >95% of cells in 6-day-old astrocyte cultures in vitro are positive for glial fibrillary acidic protein (GFAP). The primary neurons or transfected neuro 2a cells was treated in 100 ng/ml actinomycin D for 6 hours to block transcription. Then the cells were treated with C6 conditioned medium for 24 hours, as described before. The cells were harvested for further western or qRT-PCR assay.

Preparation of cell lysates and western blotting. Cultured cells transfected with or without various apoE constructs were grown to 80% confluence in six-well plates. The cells were harvested, lysed in ice-cold lysis buffer (50 mM Tris/HCl, pH 8.0, 150 mM NaCl, 0.1% SDS, 1% Nonidet p-40, 0.5% sodium deoxycholate, and a mixture of protease inhibitors) for 30 min, and centrifuged at 13,000 rpm for 15 min. Proteins in the supernatant were subjected to sodium dodecyl sulfate-polyacrylamide gel electrophoresis (SDS-PAGE) and detected by anti-apoE Western blotting.

Analyses of apoE and apoE-I3 mRNA by RT-PCR and real-time RT-PCR. Total RNA from various cell lines and mouse brains was isolated with the RNeasy Mini Kit (Qiagen) or Triazol (Invitrogen), respectively. RT-PCR of apoE and apoE-I3 was performed with 10 ng of total RNA and the RT-PCR kit from Invitrogen. All primers used in the current study are listed in Table 1.

TABLE 1

Primers Used in ApoE-I3 Studies

| Primer | Sequence |
|---|---|
| Human apoE-I3/apoE RT-PCR primers | |
| P1 (in human exon 1) | CAGCGGAGGTGAAGGACGT (SEQ ID NO: 5) |
| P2 (in human intron 3) | AGAGGCCGAGAGAAGGAGAC (SEQ ID NO: 6) |
| P3 (in human exon 4) | TTGTTCCTCCAGTTCCGATTTGTA (SEQ ID NO: 7) |
| Mouse apoE-I3/apoE RT-PCR primers | |
| P1 (in mouse exon 1) | GCTCAGACCCTGGAGGCTAA (SEQ ID NO: 8) |
| P2 (in mouse intron 3) | TGGGCTACACACTAATTGAGAAA (SEQ ID NO: 9) |
| P3 (in mouse exon 4) | CTGTTCCTCCAGCTCCTTTTTGTA (SEQ ID NO: 10) |
| Mouse apoE-I3 3'-RACE primer | |
| mApoE-2830-1 | TGCCGCAGCTTCTCAACTTCTGGGAAC (SEQ ID NO: 11) |
| Mouse apoE-I3 5'-RACE primer | |
| mApoE-2681-2 | TGGGCTACACACTAATTGAGAAA (SEQ ID NO: 12) |
| Human apoE-I3 3'-RACE primer | |
| hApoE-3499-1 | GGCTGGTCTTGAACTTCTGG (SEQ ID NO: 13) |
| Human apoE-I3 5'-RACE primer | |
| hApoE-3649-2 | AGAGGCCGAGAGAAGGAGAC (SEQ ID NO: 14) |
| Human apoE-I3 qRT-PCR primers | |
| I3-mRNA-77-1 | GCGTTGCTGGTCACATTCCT (SEQ ID NO: 15) |
| I3-mRNA-324-2 | AGGGTCAAGGGCCAGGATG (SEQ ID NO: 16) |
| Human apoE qRT-PCR primers | |
| ApoE-3F | CCCAGGTCACCCAGGAACT (SEQ ID NO: 17) |
| ApoE-4B | TCCGATTTGTAGGCCTTCAACT (SEQ ID NO: 18) |
| Human GAPDH qRT-PCR primers | |
| H-GAPDH-1 | AACAGCGACACCCATCCTC (SEQ ID NO: 19) |
| H-GAPDH-2 | CATACCAGGAAATGAGCTTGACAA (SEQ ID NO: 20) |
| Mouse GAPDH qRT-PCR primers | |
| M-GAPDH-1 | GTCTCCTGCGACTTCAGC (SEQ ID NO: 21) |
| M-GAPDH-2 | TCATTGTCATACCAGGAAATGAGC (SEQ ID NO: 22) |
| Mouse U3B snoRNA qRT-PCR primers | |
| M-U3B-1 | TGTAGAGCACCCGAAACCAC (SEQ ID NO: 23) |
| M-U3B-2 | GTCCACTCAGACTGCGTTCC (SEQ ID NO: 24) |

ApoE-I3 and apoE mRNA levels in different samples were determined in duplicate by quantitative fluorogenic reverse transcription-PCR (qRT-PCR) using GAPDH mRNA as an internal control. RT reactions were performed with Superscript First-strand Synthesis System Kits (Invitrogen, Carlsbad, Calif.) as described earlier. qRT-PCR reactions consisted of 10 µl of diluted cDNA reaction mixture (equivalent to 4.0 ng of RNA template), 12.5 µl of SYBR Green PCR master mix (Applied Biosystems), and 300 nM of each forward and backward primer in a final volume of 25 µl. Serial dilution of pooled cDNA samples from all cells or tissues were used to generate standard curves to determine the relative levels of specific mRNAs in individual samples. The apoE-I3 mRNA levels were then calculated and normalized to the internal GAPDH mRNA standards.

Kainic acid injections. Kainic acid crosses the blood-brain barrier and induces excitotoxic CNS injury, particularly in the hippocampus and neocortex. Wildtype and human apoE3 or apoE4 knock-in mice at 4-6 months of age were injected intraperitoneally with kainic acid (Sigma) dissolved in saline (0.9%) at 25 mg/kg body weight in one dose, as described. Within ~15 min, all mice developed seizures. Seizure activity was assessed as described. The groups did not differ in the time from injection to seizure onset or in the incidence, intensity, or duration of seizures. Mice were killed 1-6 days after the injection of kainic acid.

Preparation of mouse brain tissues. Brains from wildtype and human apoE isoform knock-in mice treated with or without kainic acid were collected after a 2-min transcardial perfusion with PBS. One hemibrain from each mouse was used for purifying total RNA as described above. The other hemibrain from each mouse was fixed in 3% paraformaldehyde, and paraffin sections (7 µm) were prepared. H&E and silver staining were used to access the severity of neurodegeneration of individual mouse in response to kainic acid treatment.

In situ hybridization. RNA probes specific for mouse and human apoE-I3 mRNA are complementary to nucleotides 425-580 in the intron-3 of the human apoE gene and to the nucleotides 216-374 in the intron-3 of the mouse apoE gene, respectively. RNA probes specific for mouse and human apoE mRNA are complementary to nucleotides in the mouse apoE cDNA and to the nucleotides in the human apoE cDNA, respectively, which covers both exons 3 and 4. All RNA probes were labeled with [$^{33}$P]UTP with an RNA transcription kit (Stratagene). The labeled probes were purified through Micro Bio-Spin-30 chromatography columns (Bio-Rad, Hercules, Calif.). In situ hybridization was performed as described. Briefly, brain paraffin sections (7 µm) were incubated with 20 µg/ml proteinase K (Boehringer Mannheim, Indianapolis, Ind.) in 50 mM Tris-HCl, pH 8.0, 5 mM EDTA, and 150 mM NaCl for 15 min at room temperature. Proteolytic activity was stopped by immersion for 10 min in 0.2% glycine in PBS. After fixation, acetylation, and dehydration, the sections were incubated for 14-18 h in a humidified chamber at 45° C. with labeled probes in a buffer containing 50% formamide, 300 mM NaCl, 20 mM Tris, pH 8.0, 5 mM EDTA, 0.2% polyvinylpyrrolidone, 0.02% Ficoll, 0.02% bovine serum albumin, 10% dextran sulfate, 250 µg/ml sperm DNA, and 0.1 mg/ml tRNA. After two washes at room temperature in 2×SSC and 1.0 mM EDTA for 10 min, the sections were immersed in 20 µg/ml ribonuclease (RNase) A (Sigma, St. Louis, Mo.) in 500 mM NaCl and 10 mM Tris, pH 8.0, and 10 U/ml T1 RNase (Boehringer Mannheim) for 1 h at 37° C., washed at 60° C. in six changes of 0.1×SSC with 1.0 mM EDTA for 4 h, rinsed twice for 10 min each in 0.5×SSC, and dehydrated. For dark-field and bright-field microscopy imaging, the slides were dipped in NTB2 nuclear track emulsion (Eastman Kodak, Rochester, N.Y.), incubated at 4° C. for 2-5 days, and developed with D19 developer (Eastman Kodak). The sections were then stained with hematoxylin and eosin (Fisher Scientific, Tustin, Calif.). After dehydration in a graded series of ethanol (80%, 95%, and 100%), the slides were rinsed three times in xylene and overlaid with cover slips.

Statistical Analysis A two-tailed t test assuming equal variance was used for statistical analyses. $P<0.05$ was considered significant difference.

Results

A Novel apoE-I3 Transcript in Mouse and Human Brains

To measure apoE mRNA expression in mouse brains, RT-PCR was performed with a pair of primers located in exons 1 and 4 (FIG. 1A, p1 and p3, and FIG. 1B) and control primers located in exon 1 and intron 3 (FIG. 1A, p1 and p2). Surprisingly, the control primers generated an unexpected DNA product that disappeared when the reverse transcriptase was omitted (FIG. 1B), indicating that it was a product from reverse transcription of an mRNA, but not from genomic DNA. After exclusion of primer contamination and endogenous priming (with an EndoFree RT kit, Ambion), the unexpected product was still present (not shown). Its size (~600 bp) suggested that it was not from apoE pre-mRNA containing exons 1-3 and introns 1-3 (~1.6 kb). Sequencing analysis revealed the sequences of exons 1-3 and intron 3 before primer 2 (FIG. 1A). Similar results were obtained with total RNA from human brain. Thus, the product appeared to be a splicing variant containing at least portion of the intron-3 sequence.

To identify the ends of the potential splicing variant, 3'- and 5'-RACE were used. Sequencing analyses of more than 10 clones of both 3'- and 5'-RACE products demonstrated a novel transcript that differed from apoE mRNA only by having the intron-3 retention (FIG. 1C). This "apoE-I3" transcript was present in mouse brains and at a relatively higher level in human brains as determined by RT-PCR (not shown). BLAST searches of the established sequence tag database with the human apoE intron-3 sequence identified two apoE-related sequences (AI147021 and AA902874). Both contained part of the intron 3 sequence of the apoE gene, supporting the existence of the apoE-I3 transcript.

Figure 1B:
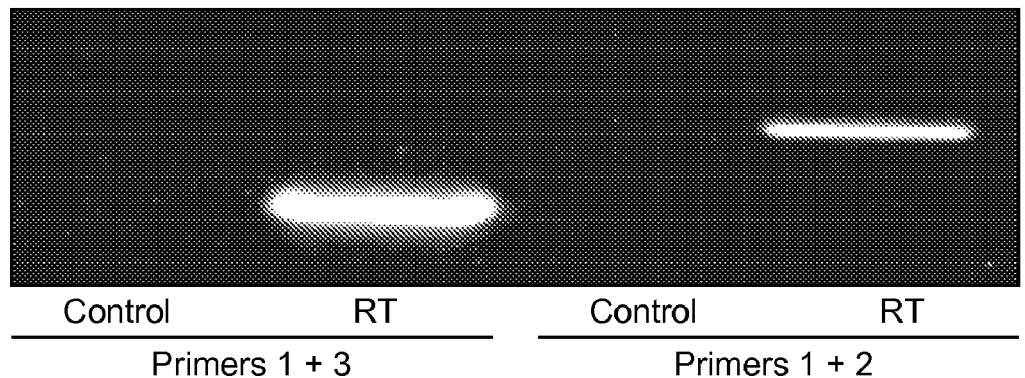
Figure 1C:
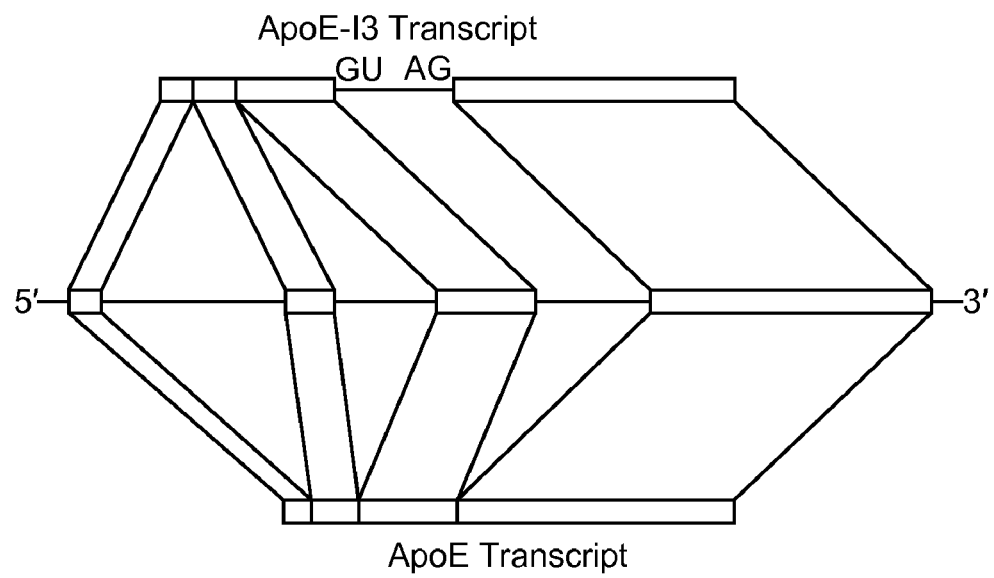

FIGS. 1A-C. Identification of apoE-I3 transcript from human and mouse brain total mRNA. (A) The apoE gene structure, including 4 exons and 3 introns, and the positions of primers 1, 2, and 3. (B) The RT-PCR results of primers 1+3 or primers 1+2 using mouse brain total RNAs as templates. Omission of the reverse transcriptase in the RT reaction was used as a negative control (CON). (C) Organization of apoE-I3 mRNA and apoE mRNA. GU and AG indicate the 5' and 3' splicing sites of intron 3 of apoE, respectively.

ApoE-I3 is Neuron-specific in CNS

RT-PCR specific for apoE-I3 revealed that it was transcribed in mouse primary cortical and hippocampal neurons (FIG. 2A) but not in mouse primary astrocytes (FIG. 2B). ApoE-I3 was also expressed in neuronal cell lines, including differentiated human NT2 neurons (FIG. 2C) and mouse neuroblastoma Neuro-2a cells, but not in astrocytic cell lines, such as human U87 (FIG. 2C). Further, as shown by real-time quantitative fluorogenic RT-PCR (qRT-PCR), significant levels of human apoE-I3 mRNA were present in Neuro-2a cells, but not C6 cells, after transfection with a human apoE genomic DNA construct containing 5 kb of 5'-flanking region, four exons, three introns, and 8 kb of 3'-flanking region of the apoE gene (FIG. 2D). In situ hybridization with apoE-I3-specific probe detected a signal highlighting the hippocampal pyramidal neurons in human apoE knock-in mice (FIG. 2E) and wildtype mice. As a negative control, pretreatment of brain sections with RNase abolished the apoE-I3 signal. Cortical neurons were also positive for apoE-I3 signal.

FIGS. 2A-E. Neuron-specific expression of apoE-I3. Neuron-specific expression of apoE-I3. (A) RT-PCR of mouse apoE-I3 and GAPDH using total RNA from mouse primary cortical or hippocampal neurons as RT templates. (B) RT-PCR of mouse apoE-I3 and GAPDH using total RNA from mouse primary neurons or primary astrocytes as RT templates. (C) RT-PCR of human apoE-I3 and GAPDH using total RNA from human NT2 neurons and U87 astrocytes as RT templates. (D) The apoE-I3 mRNA levels in Neuro-2a and C6 cells transfected with a human apoE genomic DNA construct were determined by qRT-PCR (n=5; *p<0.001 vs. N2a) (E) In situ hybridization of apoE-I3 mRNA in the hippocampus of human apoE knock-in mice.

ApoE-I3 is Retained in the Nucleus and is not Translated

Figure 3:
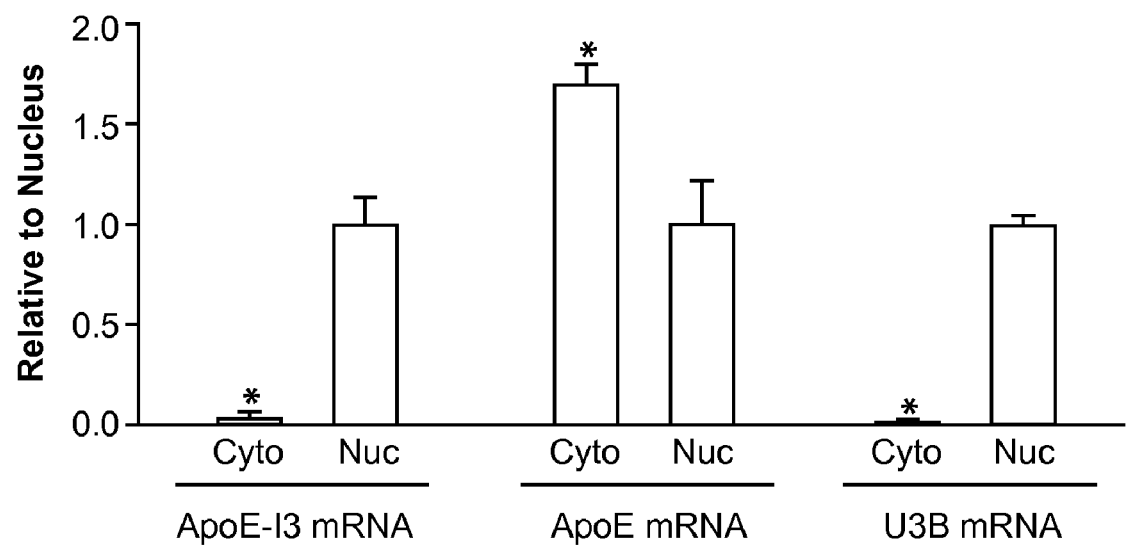
FIG. 3 depicts retention of apoE-I3 in the nucleus.

In Neuro-2a cells stably transfected with an apoE genomic DNA, >98% of apoE-I3 mRNA was retained in the nucleus, as shown by qRT-PCR, whereas ~60% of apoE mRNA was in the cytosol (FIG. 3). Importantly, >98% of U3B small nucleolar mRNA was also found in the nuclear fraction (FIG. 3), ascertaining the purity of nuclear and cytosolic fractions (Speckmann et al., 1999). The potential protein sequence encoded by apoE-I3 mRNA was examined. Since there is a stop codon at the junction of exon 3 and intron 3 in the apoE-I3 transcript, the expected translation product was a short peptide containing the first 60 amino acids of apoE. Extensive anti-apoE western blotting with various polyclonal and monoclonal antibodies, which recognize the N-terminus of apoE, failed to reveal such a peptide in different neuronal cells transfected with or without apoE genomic DNA or in mouse and human brains.

FIG. 3. The apoE-I3 mRNA is retained in the nucleus. The apoE-I3 mRNA levels in the nuclei (Nuc) and cytosol (Cyto) of Neuro-2a cells transfected with a human apoE genomic DNA construct were determined by qRT-PCR (n=3; *p<0.001 vs. Nucleus). The apoE mRNA levels in the nuclei and cytosol of Neuro-2a cells transfected with a human apoE genomic DNA construct were determined by qRT-PCR (n=3; *p<0.01 vs. Nucleus). The U3B small nucleolar mRNA levels in the nuclei and cytosol of Neuro-2a cells used above were determined by qRT-PCR (n=3; *p<0.001 vs. Nucleus).

Intron-3 Retention/Splicing Controls Neuronal Expression of apoE

To determine the role of intron 3 in neuronal expression of apoE, apoE expression in Neuro-2a cells transfected with a cDNA or a genomic DNA construct was measured (FIG. 4A). ApoE was expressed at much higher levels in cells transfected with cDNA (FIG. 4B, C), while apoE-I3 was expressed only in cells transfected with genomic DNA (FIG. 4B). When intron 3 was deleted from the apoE genomic DNA construct (apoE4-ΔI3) (FIG. 4D), apoE expression was 4-5-fold higher in Neuro-2a and rat primary hippocampal neurons transfected with that construct than in cells transfected with the wildtype apoE4 genomic DNA construct (FIG. 4D). When intron 3 was inserted into the apoE cDNA (apoE-I3-cDNA), the apoE expression level in cells transfected with that construct was ~30% of that in cells transfected with wildtype apoE-cDNA. Thus, intron 3 is associated with a low level of apoE expression in neuronal cells.

FIGS. 4A-D. Intron-3 retention/splicing controls neuronal expression of apoE. (A) Schematic models of human apoE cDNA and genomic DNA constructs. (B) RT-PCR of human apoE-I3 and apoE using total RNA isolated from Neuro-2a cells transfected with a human apoE4 cDNA or a genomic DNA construct as templates. (C) ApoE western blotting of cell lysates from Neuro-2a cells transfected with a human apoE4 cDNA or a genomic DNA construct. (D) The human apoE4 or apoE4-ΔI3 genomic DNA construct was transfected into Neuro-2a or rat primary hippocampal neurons. The intracellular apoE protein levels were determined by anti-apoE western blotting and compared by calculating the ratio of apoE protein in apoE4-ΔI3-transfected cells to that in apoE4-transfected cells (N2a, 4±1, n=6; primary neuron, 5±1, n=6).

Astroglial Regulation of Neuronal apoE Expression Acts Through the Processing of apoE-I3

Figure 5A:
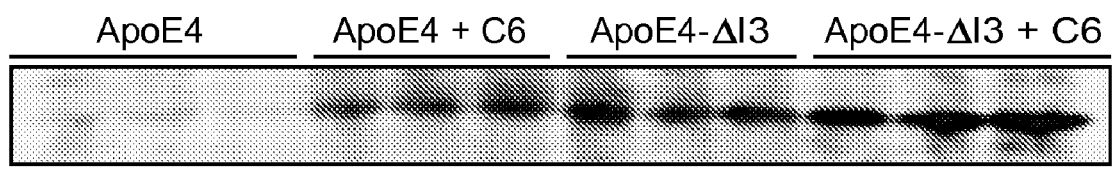
FIGS. 5A-C depict regulation of neuronal apoE-I3 expression by processing of apoE-I3.
Figure 5B:
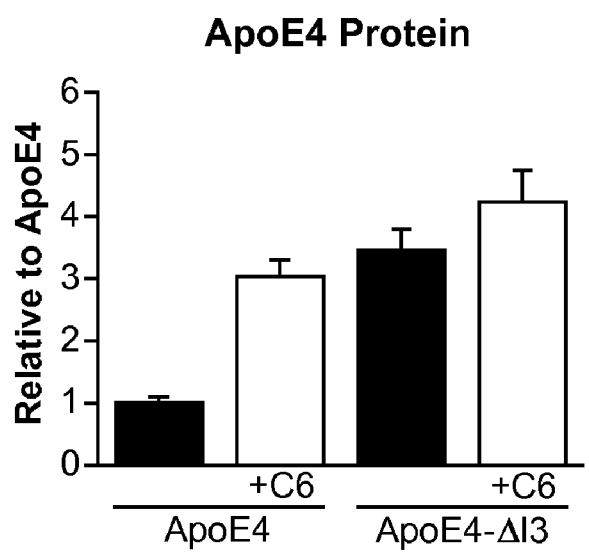

Previously, it was shown that astrocyte-conditioned medium upregulates apoE expression in transfected Neuro-2a cells and mouse primary neurons (FIG. 5A, six left lanes, and FIG. 5B) (Harris et al. (2004) J Biol Chem 279:3862-3868). However, astrocyte-conditioned medium did not significantly alter apoE promoter activity in an alkaline phosphatase reporter assay (FIG. 5C), and removal of intron 3 from the apoE genomic DNA abolished the regulatory role of the conditioned medium (FIG. 5A, six right lanes, and FIG. 5B). Thus, upregulation of neuronal apoE expression by an astrocytic factor (or factors) likely reflects increased processing of apoE-I3.

Figure 5C:
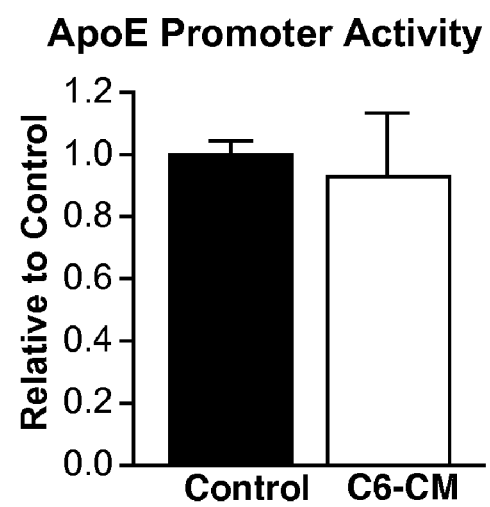

FIGS. 5A-C. Astroglial regulation of neuronal apoE expression acts through the processing of apoE-I3. (A) Neuro-2a cells were transfected with apoE4 or apoE4-ΔI3 genomic DNA construct in the presence or absence of C6-conditioned medium. The cells were lysed 24 h after transfection as described in Materials and Methods. The same amounts of total proteins were subjected to SDS-PAGE and detected by anti-apoE western blotting. (B) Quantitative results of A, as determined by scanning the apoE bands, were reported as relative to apoE4 (n=3). (C) The effect of astrocyte-conditioned medium on apoE promoter activity was determined in Neuro-2a cells stably transfected with an apoE promoter-alkaline phosphatase reporter construct (n=9).

Figure 6A:
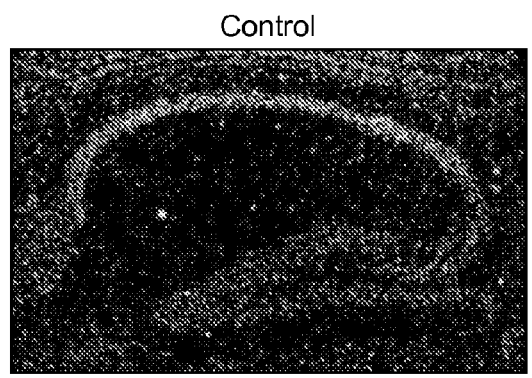
FIGS. 6A-D depict expression of apoE-I3 in mouse brains in response to excitotoxic injury.
Figure 6B:
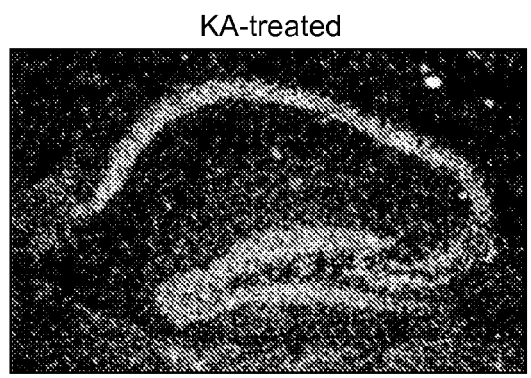
Figure 6C:
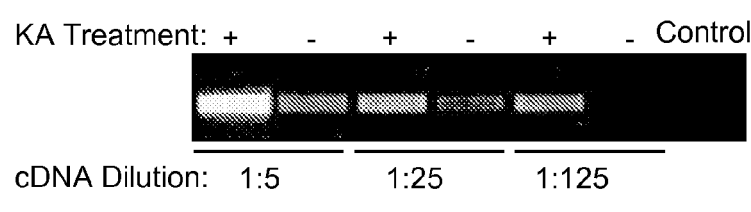
Figure 6D:
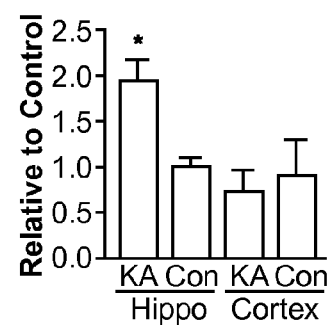

Expression and Processing of apoE-I3 is Regulated by Neuronal Injury in the Hippocampus To determine if apoE-I3 processing is involved in the control of apoE expression by neurons in response to excitotoxic injury (Boschert et al. (1999) Neurobiol Dis 6:508-514; Xu et al. (2006) J Biol Chem 275:31770-31777), human apoE knock-in mice were treated with kainic acid and assessed neuronal injury by H&E and silver staining. In situ hybridization demonstrated that excitotoxic stress dramatically increased apoE-I3 mRNA levels in morphologically normal hippocampal neurons (FIG. 6A, B). RT-PCR analyses using a serial dilution of cDNA templates demonstrated higher levels of apoE-I3 mRNA in the brains of treated mice than in controls (FIG. 6C). qRT-PCR demonstrated a twofold increase of apoE-I3 expression in the hippocampus, but not in the cortex (FIG. 6D).

Figures 7A, 7B:
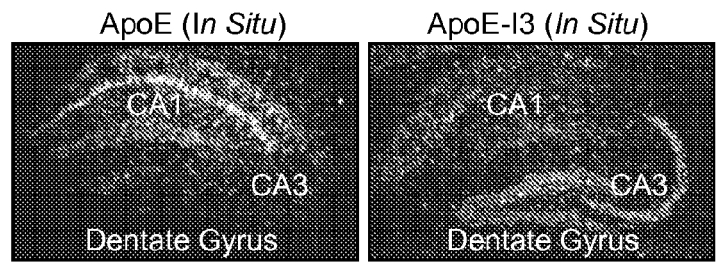
FIGS. 7A-F depict inverse correlation of apoE-I3 expression to apoE expression in mouse hippocampus in response to excitotoxic injury.
Figure 7C:
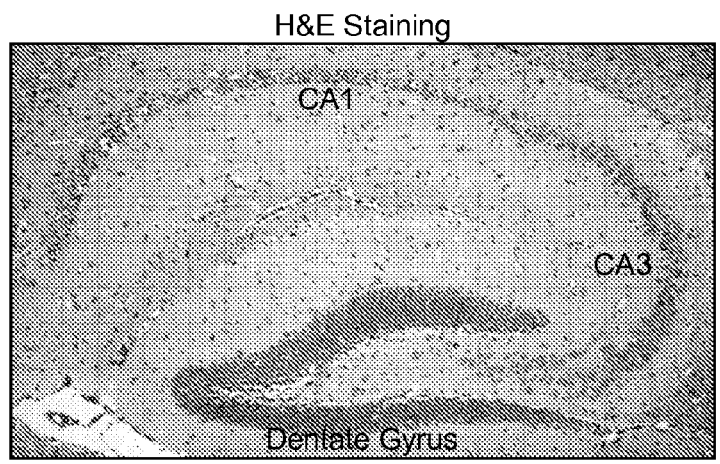

In degenerating hippocampal CA1 neurons in the treated mice, however, apoE-I3 mRNA disappeared, although it was still present in uninjured CA3 neurons and dentate gyrus granular cells (FIG. 7B, C). In contrast, apoE mRNA was clearly present in the degenerating CA1 neurons but not in CA3 and dentate gyrus granular cells (FIG. 7A, C). Thus, in response to excitotoxic stress, apoE-I3 expression increased in neurons with normal morphology but disappeared in degenerating neurons. Conversely, apoE mRNA was expressed in degenerating neurons but not in normal neurons, as reported (Xu et al., 2006).

Figure 7D:
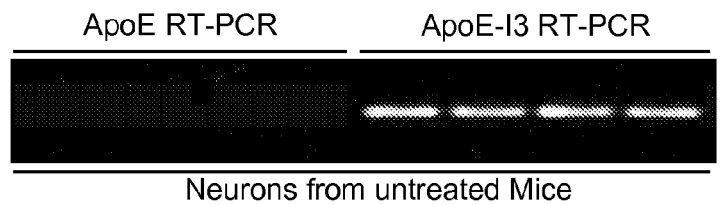
Figure 7E:
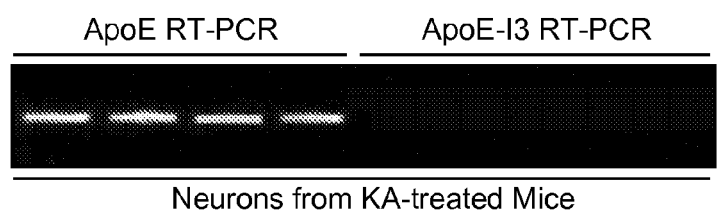
Figure 7F:

The expression of apoE-I3 and apoE mRNA was compared by RT-PCR in CA1 neurons collected by laser capture microdissection from untreated and kainic acid-treated apoE4/EGFP$_{apoE}$ reporter mice, in which one apoE allele is targeted apoE4 and the other is targeted EGFP (Xu et al., 2006, supra). In these mice, neurons express EGFP and apoE in response to injury (Xu et al., 2006, supra). The EGFP-negative CA1 neurons collected from untreated apoE4/EGFP$_{apoE}$ mice by laser capture microdissection expressed apoE-I3 mRNA, but not apoE mRNA, as determined by RT-PCR (FIG. 7D). However, the EGFP-positive CA1 neurons collected from kainic acid-treated apoE4/EGFP$_{apoE}$ mice expressed apoE mRNA, but not apoE-I3 mRNA (FIG. 7E). Importantly, both cells expressed similar levels of GAPDH (FIG. 7F), ascertaining the quality of RNA and an appropriate RT-PCR reaction, and did not express GFAP, suggesting no significant contamination of astrocytes. Thus, apoE-I3 and apoE mRNA levels are inversely correlated in neurons in vivo.

FIGS. 6A-D. Expression of apoE-I3 in mouse brains in response to excitotoxic injury induced by kainic acid (KA). (A, B) In situ hybridization of apoE-I3 mRNA in control (A) and kainic acid-treated (B) human apoE knock-in mice. (C) RT-PCR of apoE-I3 using a serial dilution of total RNA from the brains of kainic acid-treated and untreated mice as templates. (D) qRT-PCR of apoE-I3 in the hippocampus and cortex of control (Con) and kainic acid-treated (KA) mice (n=3; *p<0.001 vs. the corresponding control).

FIGS. 7A-F. ApoE-I3 expression is inversely correlated with apoE expression in mouse hippocampus in response to excitotoxic injury. (A) In situ hybridization of apoE mRNA showed positive signals in injured CA1 neurons in a kainic acid-treated mouse. (B) In situ hybridization of apoE-I3 mRNA showed the opposite pattern to that of apoE mRNA (e.g., negative signals of apoE-I3 mRNA in degenerating CA1 neurons). (C) H&E staining showed neurodegeneration in the CA1 region but not in CA3 or the dentate gyrus. (D) RT-PCR of apoE and apoE-I3 in EGFP-negative CA1 neurons collected from untreated apoE4/EGFP$_{apoE}$ reporter mice (n=4) by laser capture microdissection. (E) RT-PCR of apoE and apoE-I3 in EGFP-positive CA1 neurons collected from kainic acid-treated apoE4/EGFP$_{apoE}$ mice (n=4) by laser capture microdissection. (F) RT-PCR of GAPDH in EGFP-negative and EGFP-positive CA1 neurons collected from untreated and kainic acid-treated apoE4/EGFP$_{apoE}$ mice (n=4), respectively, by laser capture microdissection.

ApoE-I3 is Likely a Precursor of apoE mRNA

Figure 8A:
FIGS. 8A-D depict results showing that ApoE-I3 is a precursor of apoE mRNA.
Figure 8B:
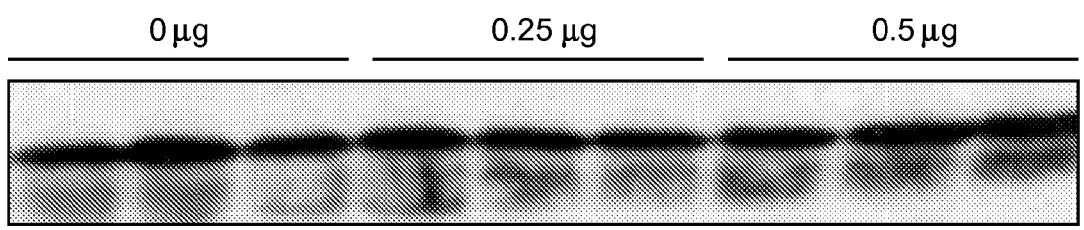

It was then determined whether apoE-I3 functions as a noncoding RNA that regulates neuronal expression of apoE or as a precursor of apoE mRNA. First, the splicing acceptor site of intron 3 in the apoE-I3-cDNA construct was mutated to eliminate the splicing of intron 3 (FIG. 8A). In transfected Neuro-2a cells, this mutant construct was transcribed into an mRNA with intron-3 retention, without protein translation. Importantly, apoE expression was not significantly altered by transfection of the mutant construct at different doses into Neuro-2a cells stably expressing apoE4 from a genomic DNA construct (FIG. 8A, B). Thus, it is unlikely that apoE-I3 is a noncoding RNA that regulates neuronal expression of apoE.

Figure 8C:
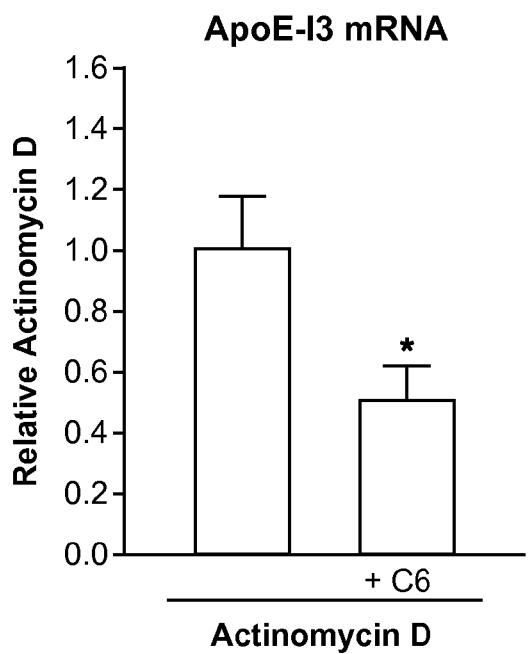
Figure 8D:
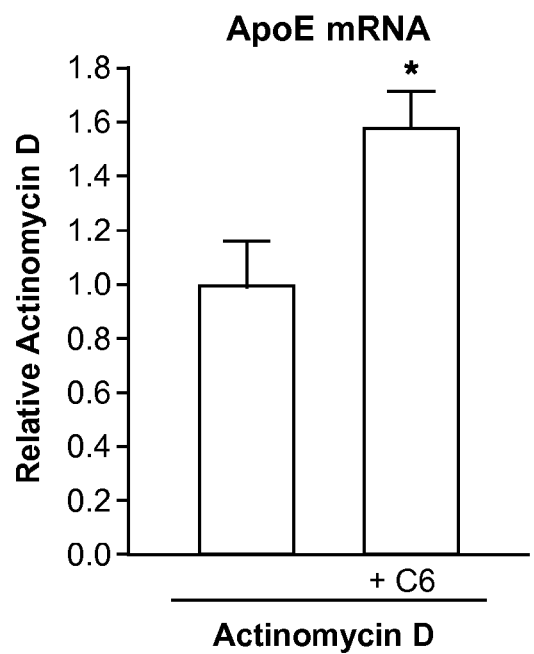

To determine if apoE-I3 is a precursor of apoE mRNA, we cultured primary hippocampal neurons from human apoE4 knock-in mice for 14 days, treated them with the transcription inhibitor actinomycin D for 6 h, and induced apoE expression with astrocyte-conditioned medium. ApoE-I3 mRNA levels decreased and apoE mRNA levels increased, despite the transcription inhibition (FIG. 8C, D). These results suggest that apoE-I3 is likely a precursor of apoE mRNA and that the astrocyte-derived factor (or factors) upregulates neuronal expression of apoE by stimulating the processing of apoE-I3 into apoE mRNA.

FIGS. 8A-D. ApoE-I3 is a precursor of apoE mRNA. (A) A schematic model of an unsplicable apoE-I3 cDNA construct, in which the splicing acceptor site of intron 3 was mutated to eliminate the splicing. (B) Neuro-2a cells stably expressing apoE4 from a wildtype genomic DNA construct were transfected with different amounts of the unsplicable apoE-I3 cDNA construct. Intracellular apoE protein levels were determined by anti-apoE western blotting 24 h after transfection. (C, D) Primary hippocampal neurons from human apoE4 knock-in mice were cultured in vitro for 14 days and then treated with the transcription inhibitor actinomycin D for 6 h, and apoE expression was then induced with astrocyte-conditioned medium. The levels of apoE-I3 (C) and apoE (D) mRNA were quantified by qRT-PCR (n=6; *p<0.01 vs. Actinomycin D).

Figure 9:
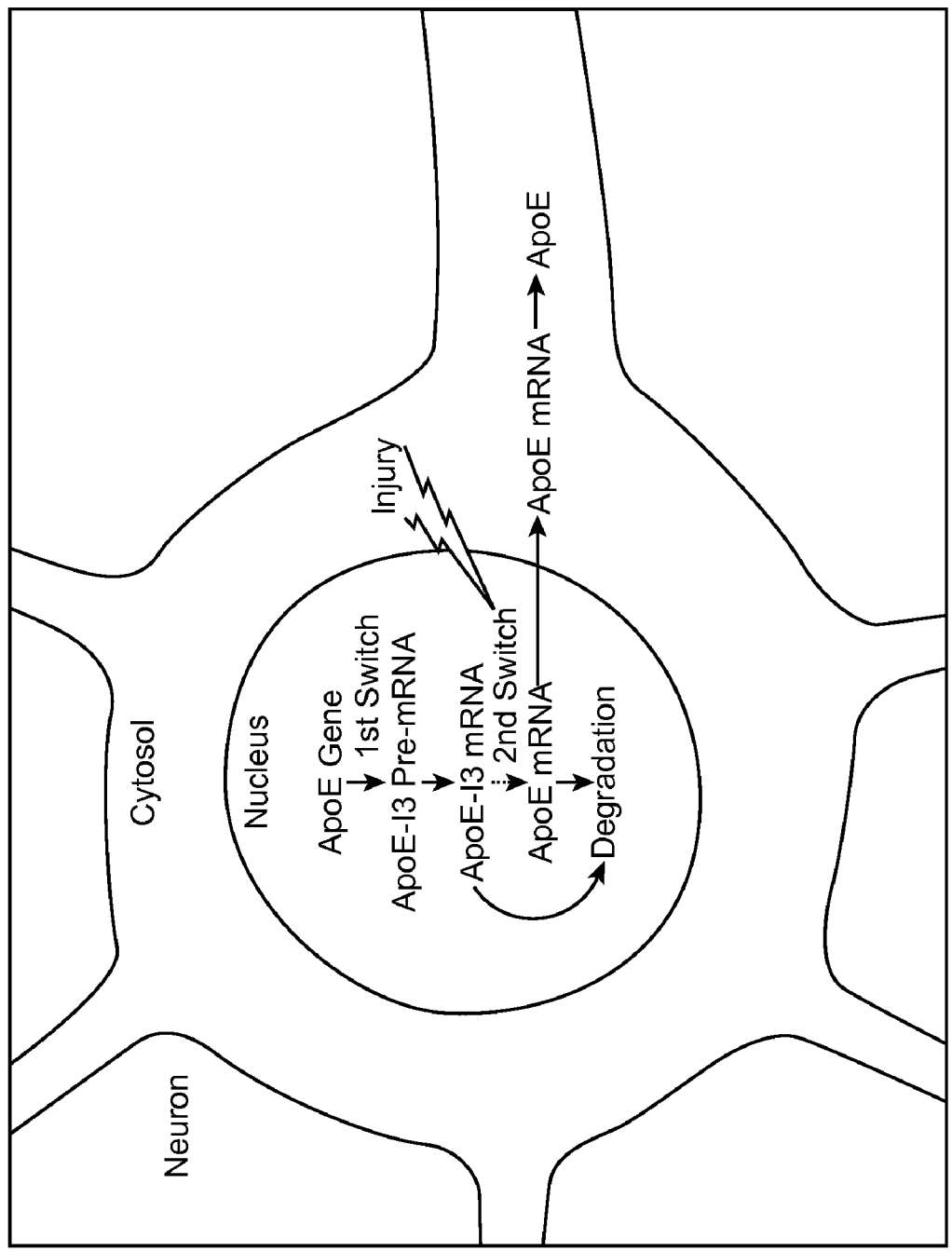
FIG. 9 schematically depicts a two-switch model for the control of neuronal expression of apoE.

FIG. 9. A "two-switch" model for the control of neuronal expression of apoE. The first switch—transcription of the apoE gene—is constitutively on and generates apoE-I3 under normal conditions. The apoE-I3 is retained in the nucleus and is not translated. The second switch—the processing of apoE-I3 into mature apoE mRNA—is turned on in response to neuronal injury.

Example 2

A Reporter Assay for Intron-3 Retention/Splicing in Neuronal Cells

A reporter assay in neuronal cells was developed to monitor apoE intron-3 splicing activity. An EGFP reporter construct (apoE-I3-EGFP, FIG. 11A) was created; this reporter construct was stably transfected into Neuro-2a cell. Owing to the lack of ability to splice intron 3 from apoE-I3-EGFP mRNA, Neuro-2a cells generated very low (baseline) levels of apoE-EGFP fusion protein, as determined by flow cytometry (FIG. 11B). When astrocyte-conditioned medium was added, intron-3 splicing increased, resulting in the expression of high levels of the apoE-EGFP fusion protein (FIG. 11B). Transfection of the same construct into astrocytic C6 cells resulted in very high and unchanged expression of the apoE-EGFP fusion protein, suggesting neuron-specificity of the reporter system. The stable Neuro-2a cells carrying the apoE-I3-EGFP reporter construct was cultured in 96-well plates; and a FlexStation III fluorescent plate reader (Molecular Devices) was used to measure the change in EGFP fluorescence intensity in response to various stimuli. Thus, a cell-based reporter assay for measuring intron-3 retention/splicing activity in neuronal cells in vitro was established.

Figure 11A:
FIGS. 11A and 11B depict a reporter assay for intron-3 retention/splicing in neuronal cells.
Figure 11B:
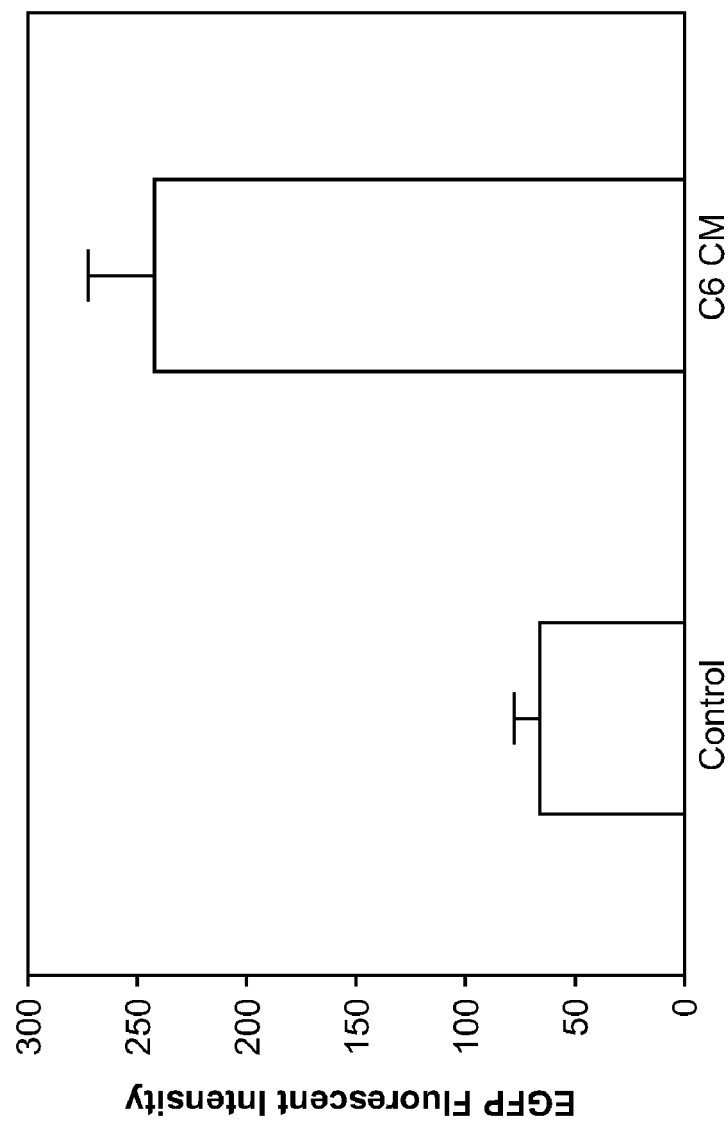

FIGS. 11A and 11B. Neuro-2a cell-based apoE-I3-EGFP reporter assay. (A) An apoE-I3 splicing reporter construct in which an EGFP cDNA was fused to the 3' end of the apoE-I3 cDNA construct (apoE-I3-EGFP). (B) EGFP fluorescence intensity in Neuro-2a cells stably expressing apoE-I3-EGFP treated without (Control) or with C6-conditioned medium (C6 CM) for 24 h, as determined by flow cytometry (n=6).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated nucleic acid comprising a nucleotide sequence having at least 95% nucleotide sequence identity to the nucleotide sequence set forth in SEQ ID NO: 1.

2. The nucleic acid of claim 1, wherein the nucleotide sequence is operably linked to a promoter.

3. The nucleic acid of claim 2, wherein the promoter is a constitutive promoter.

4. The nucleic acid of claim 2, wherein the promoter is a neuron-specific promoter.

5. A recombinant construct comprising the nucleic acid of claim 1.

6. A genetically modified host cell comprising the recombinant construct of claim 5.

7. The host cell of claim 6, wherein the host cell is a prokaryotic cell.

8. The host cell of claim 6, wherein the host cell is a eukaryotic cell.

9. The host cell of claim 8, wherein the host cell is a primary neuron.

10. The host cell of claim 8, wherein the host cell is a neuronal cell line.

11. The nucleic acid of claim 1, wherein the nucleic acid is synthetic.

12. The nucleic acid of claim 1, wherein the nucleic acid is a cDNA.

* * * * *